(12) United States Patent
Holzrichter et al.

(10) Patent No.: US 7,191,105 B2
(45) Date of Patent: *Mar. 13, 2007

(54) CHARACTERIZING, SYNTHESIZING, AND/OR CANCELING OUT ACOUSTIC SIGNALS FROM SOUND SOURCES

(75) Inventors: John F. Holzrichter, Berkeley, CA (US); Lawrence C. Ng, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 913 days.

This patent is subject to a terminal disclaimer.

(21) Appl. No.: 10/350,393

(22) Filed: Jan. 22, 2003

(65) Prior Publication Data

US 2003/0149553 A1 Aug. 7, 2003

Related U.S. Application Data

(63) Continuation-in-part of application No. 09/205,159, filed on Dec. 2, 1998, now Pat. No. 6,542,857.

(51) Int. Cl.
*G06F 7/60* (2006.01)
*G10L 19/08* (2006.01)

(52) U.S. Cl. .......................... 703/2; 702/104; 704/207; 704/236; 704/270.1; 704/223

(58) Field of Classification Search ................ 703/2; 704/207, 272, 223, 236, 270.1; 381/66, 71.4; 702/104

See application file for complete search history.

(56) References Cited

U.S. PATENT DOCUMENTS

| | | | |
|---|---|---|---|
| 2,823,365 A | 2/1958 | Rines | |
| 4,018,121 A | 4/1977 | Chowning | |
| 4,321,852 A | 3/1982 | Young, Jr. | |
| 4,343,969 A | 8/1982 | Kellett | |

(Continued)

FOREIGN PATENT DOCUMENTS

EP 0 308 526 B1 2/1992

(Continued)

OTHER PUBLICATIONS

P. A. Nelson, et al., "Active Noise Control," Encyclopedia of Acoustics, 1997, chapter 84, John Wiley & Sons, Inc., pp. 1025-1037.

(Continued)

*Primary Examiner*—Thai Phan
(74) *Attorney, Agent, or Firm*—Eddie E. Scott

(57) ABSTRACT

A system for characterizing, synthesizing, and/or canceling out acoustic signals from inanimate and animate sound sources. Electromagnetic sensors monitor excitation sources in sound producing systems, such as animate sound sources such as the human voice, or from machines, musical instruments, and various other structures. Acoustical output from these sound producing systems is also monitored. From such information, a transfer function characterizing the sound producing system is generated. From the transfer function, acoustical output from the sound producing system may be synthesized or canceled. The systems disclosed enable accurate calculation of transfer functions relating specific excitations to specific acoustical outputs. Knowledge of such signals and functions can be used to effect various sound replication, sound source identification, and sound cancellation applications.

4 Claims, 12 Drawing Sheets

U.S. PATENT DOCUMENTS

| | | |
|---|---|---|
| 4,401,855 A | 8/1983 | Broderson et al. |
| 4,653,102 A | 3/1987 | Hansen |
| 4,862,503 A | 8/1989 | Rothenberg |
| 5,029,509 A | 7/1991 | Serra et al. |
| 5,111,727 A | 5/1992 | Rossum |
| 5,171,930 A | 12/1992 | Teaney |
| 5,248,845 A | 9/1993 | Massie et al. |
| 5,251,262 A | 10/1993 | Suzuki et al. |
| 5,326,349 A | 7/1994 | Baraff |
| 5,327,521 A * | 7/1994 | Savic et al. .................. 704/272 |
| 5,345,471 A | 9/1994 | McEwan |
| 5,361,070 A | 11/1994 | McEwan |
| 5,408,911 A | 4/1995 | Weiss et al. |
| 5,448,645 A | 9/1995 | Guerci |
| 5,448,904 A | 9/1995 | Zuckerwar et al. |
| 5,454,375 A | 10/1995 | Rothenberg |
| 5,473,726 A | 12/1995 | Marshall |
| 5,512,834 A | 4/1996 | McEwan |
| 5,517,571 A | 5/1996 | Saruta et al. |
| 5,522,013 A | 5/1996 | Vanska |
| 5,528,726 A | 6/1996 | Cook |
| 5,572,791 A | 11/1996 | Kojima |
| 5,573,012 A | 11/1996 | McEwan |
| 5,587,548 A | 12/1996 | Smith, III |
| 5,602,959 A | 2/1997 | Bergstrom et al. |
| 5,659,658 A | 8/1997 | Vanska |
| 5,682,164 A | 10/1997 | McEwan |
| 5,698,807 A | 12/1997 | Massie et al. |
| 5,704,007 A | 12/1997 | Cecys |
| 5,717,828 A | 2/1998 | Rothenberg |
| 5,729,694 A | 3/1998 | Holzrichter et al. |
| 5,744,742 A | 4/1998 | Lindemann et al. |
| 5,766,208 A | 6/1998 | McEwan |
| 5,794,203 A | 8/1998 | Kehoe |
| 5,805,110 A | 9/1998 | McEwan |
| 5,825,894 A | 10/1998 | Shennib |
| 6,006,175 A | 12/1999 | Holzrichter |
| 6,073,100 A | 6/2000 | Goodridge, Jr. |
| 6,092,039 A | 7/2000 | Zingher |
| 6,122,609 A | 9/2000 | Scalart et al. |
| 6,167,138 A | 12/2000 | Shennib |
| 6,285,979 B1 | 9/2001 | Ginzburg et al. |
| 6,304,846 B1 | 10/2001 | George et al. |
| 6,327,562 B1 | 12/2001 | Proust |
| 6,377,919 B1 | 4/2002 | Burnett et al. |
| 6,381,572 B1 | 4/2002 | Ishimitsu et al. |
| 6,542,857 B1 * | 4/2003 | Holzrichter et al. ........... 703/2 |
| 6,556,682 B1 * | 4/2003 | Gilloire et al. ............... 381/66 |
| 2003/0026437 A1 * | 2/2003 | Janse et al. ................ 381/71.4 |

FOREIGN PATENT DOCUMENTS

| | | |
|---|---|---|
| EP | 0 671 610 B1 | 5/2000 |
| WO | PCT WO 97/29481 | 8/1997 |
| WO | PCT WO 97/43729 | 11/1997 |
| WO | PCTUS 99 28563 | 3/2000 |

OTHER PUBLICATIONS

L. R. Rabiner, et al., "Digital Processing of Speech Signals," 1978, Bell Laboratories, Inc., Prentice-Hall Signal Processing Series, pp. 78-85.

Parsons, Thomas W., "Linear Prediction," Chapter 6 Linguistic and Technical Fundamentals, 1987, pp. 136-145.

T. E. McEwan, "Namm '96 Trip Report," Lawrence Livermore National Laboratory, Jan. 19, 1995, 2 pages.

Ray D. Kent et al., "The Acoustic Analysis of Speech," Singular Publishing Group, Inc., 1992, pp. 72-86.

* cited by examiner

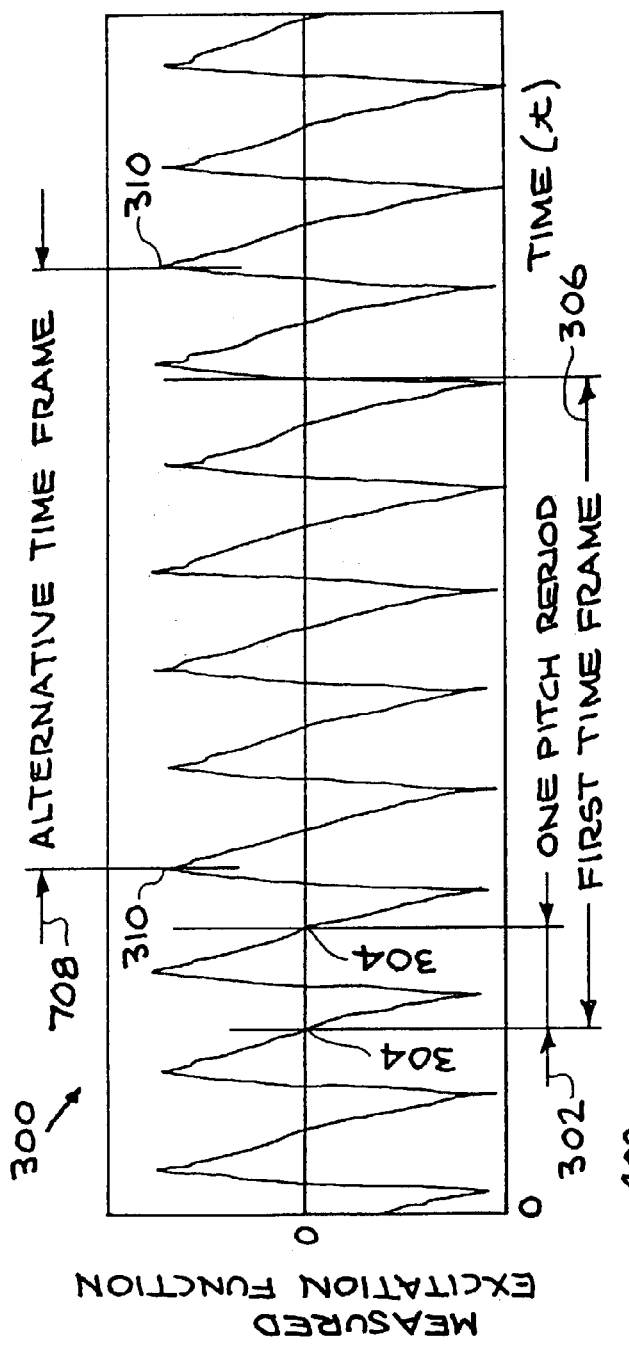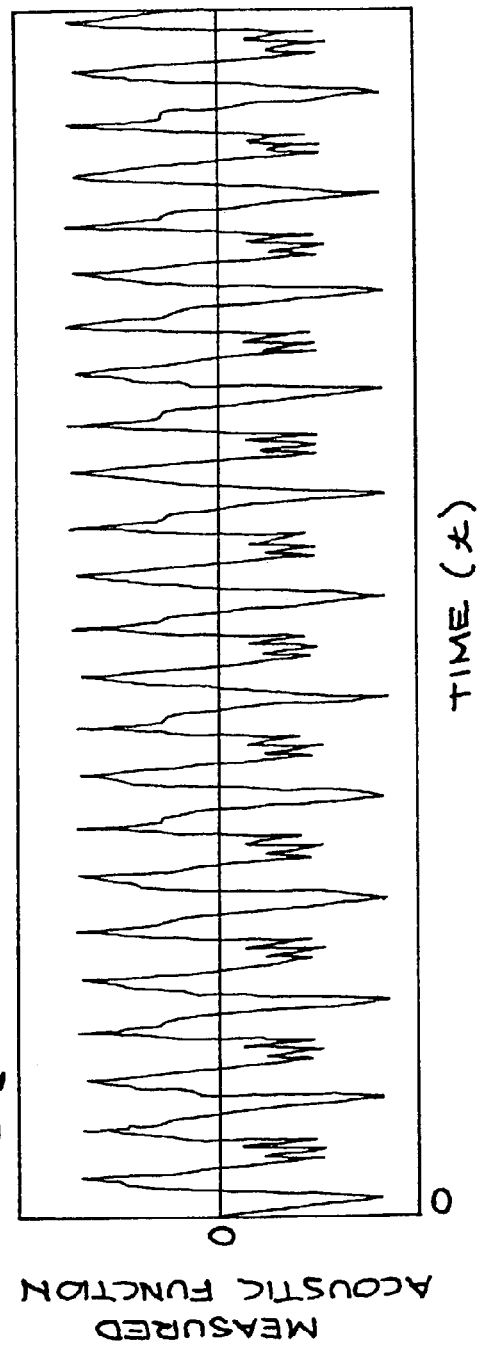
FIG. 3
FIG. 4

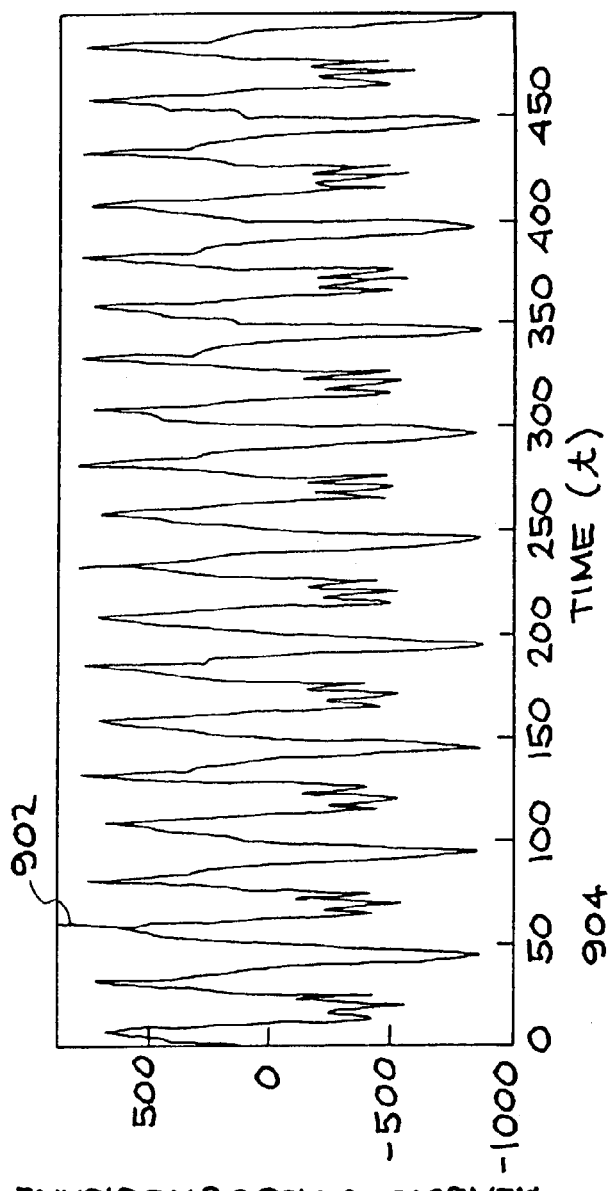
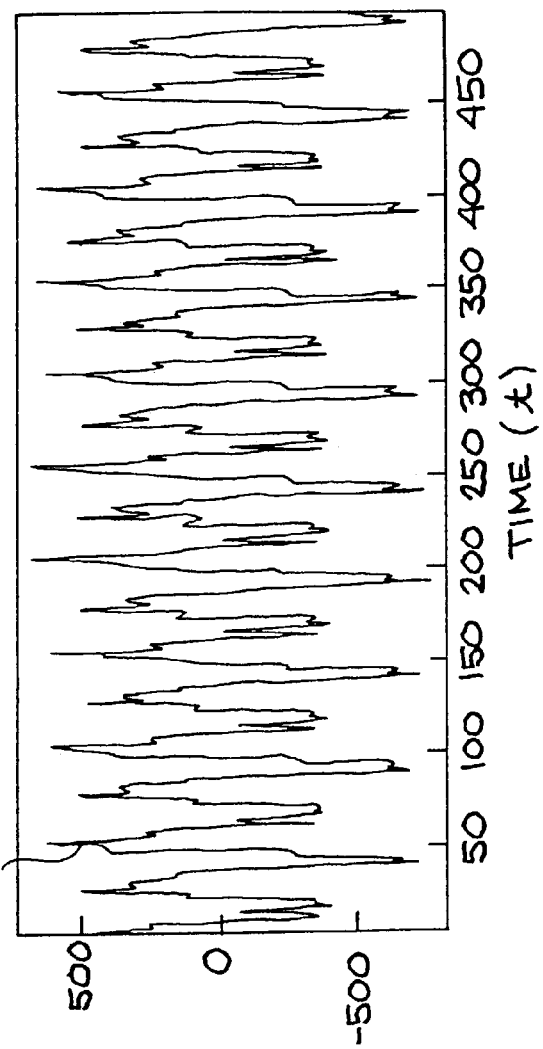
FIG.9A
FIG.9B

CHARACTERIZING, SYNTHESIZING, AND/OR CANCELING OUT ACOUSTIC SIGNALS FROM SOUND SOURCES

CROSS-REFERENCE TO RELATED APPLICATIONS

This application is a Continuation-in-Part of U.S. patent application Ser. No. 09/205,159 filed Dec. 2, 1998 now U.S. Pat. No. 6,542,857, and titled "System and Method for Characterizing, Synthesizing, and/or Canceling Out Acoustic Signals From Inanimate Sound Sources," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to systems and methods for characterizing, synthesizing, and/or canceling out acoustic signals from sound sources, including animate sound sources, and more particularly for using electromagnetic and acoustic sensors to perform such tasks.

2. Discussion of Background Art

Sound characterization, simulation, and cancellation are very important ongoing fields of research and commercial practice. Sound sources range from pleasant sounding musical instruments to very harsh and possibly harmful sounds from engines, air ducts, machines, and/or heavy equipment. Modem recording systems analyze and characterize sound sources, synthesizers use this characterized data to attempt to mimic various musical instruments, and noise cancellation technology uses prior analyzed data to reduce undesired sound levels.

Two prior art methods are in use today for analyzing and synthesizing sounds. The first method records long time duration segments of a sound, then divides them into shorter "segments." During synthesis, the segments are arranged and concatenated as needed to synthesize a desired sound sequence. Such methods are often used to simulate musical instruments, as described in U.S. Pat. No. 5,111,727 entitled, "Digital sampling instrument for digital audio data" by D. P. Rossum. The second method of sound analysis and synthesis involves using measured or simulated sound system elements, such as sine waves, which are processed and modified for play back as desired. A prior art analog system of this nature is described in U.S. Pat. No. 4,018,121 entitled, "Method of synthesizing a musical sound" by J. M. Chowning. However, a shortcoming of these two prior art methods is that they do not use excitation source information to analyze, synthesize, and cancel sounds that sound producing objects make.

FIG. 1 is a dataflow diagram of a third prior art sound analysis and synthesis system. The third system is typical of those currently used in digital musical synthesizers and is further described in U.S. Pat. No. 5,029,509 entitled, "Musical synthesizer combining deterministic and stochastic waveforms" by X. Serra and J. Smith. To begin, a sound signal 102 is recorded from an acoustic microphone. In step 104, a time frame is set and a fundamental pitch is determined for the sound signal 102, in step 106. Next in step 108, one or more sine wave functions are generated with the same time frame and harmonic relationships as the sound signal 102. The sine functions are fitted, in step 109, to the sound signal 102 and, in step 110, a corresponding set of amplitudes, phases, and frequencies for the sine functions are stored in memory 112. The sine functions, best fit by one or more harmonic waves, are then subtracted from the sound signal 102 to generate a residual acoustic signal 114. The residual signal 114 is then fitted 116 to a white noise signal from a white noise generator 118. The white noise signal can be further characterized using a Linear Predictive Coding (LPC) technique, also called an all-pole method technique. Next in step 120, coefficients that fit the noise signal to the residual signal 114 are stored in the memory 112 and are recalled on command.

As a first step in synthesizing the sound signal 102, MIDI or other sound control systems call for the needed sequence of amplitude, pitch, attack, reverberation, and other control variables 122. Next, in step 126, the coefficients stored in the memory in step 120 that describe the sine and residuals are modified to generate variations of the stored sounds, according to the user's control description. In step 128, sequences of sine functions describing the harmonic aspects of the desired synthesized signal are added together. The functions describing the residual signal 114 are added to the summed harmonic functions to make a single time frame of a sound sequence signal 130. Finally, sequential frames are added together to make a multiframe sound sequence signal 130, which is then amplified through a speaker 132 for a listener 134 to hear. Ideally the multiframe sound sequence signal 130 is as close a match as possible to the original sound signal 102.

A variant on the third prior art method is described in U.S. Pat. No. 5,587,548 entitled, "Musical Tone Synthesis System Having Shortened Excitation Table," by Smith. Smith describes how to use previously measured sound excitations, usually obtained by impulsive excitation of body modes, to synthesize a musical sound. In addition, Smith uses computed "loops" whose cycle rate defines pitch values for synthesized sound. This process is called "physical modeling synthesis." This process often uses simplified functional descriptions of vibrating mechanical elements to describe the mechanics of string motions, their coupling to the body via a bridge, and to resonator panels in musical instruments.

None of these prior art methods accurately captures qualities of sound sources because they are only based upon approximating an output signal, or intermediate process, and fail to accurately characterize the underlying physical processes of sound generation and their collective behavior. Such methods also have difficulty defining time frames based upon a natural cycle of the sound sources, and in forming accurate transfer functions and associated filters, especially in high noise environment. As a result, prior art methods are not able to accurately synthesize human voices and well-known musical instruments, such as Steinway pianos, Stradivarius violins, ebony clarinets, and other fine instruments to the degree desired. In addition, these prior art analysis methods tend to not work well in real time sound cancellation applications.

Separate from the three methods described above, hybrid sound generators, such as are used in electric guitars, generate sounds by monitoring excitation sources, such as strings on a musical instrument. In these hybrid instruments, acoustic sounds from the musical instrument itself are usually ignored. U.S. Pat. No. 5,572,791 entitled, "Method for positioning a pickup on an electric guitar" by K. Kazushige and U.S. Pat. No. 4,321,852 entitled, "Stringed instrument synthesizer apparatus" by L. D. Young Jr. describes these techniques and methods in more detail. As a result, typical guitar string sensors only measure approximate excitations of the musical instrument, which are then fed to an amplifier, filter bank, and loud speaker.

The prior art methods of sound analysis and synthesis are also applied to the problem of canceling out undesirable sounds. These methods are described in references such as the *Encyclopedia of Acoustics*, Vols. I–IV, M. J. Crocker ed., Wiley, N.Y. 1997; Vol. II chapters 79–89 and Vol. IV chapters 130–139, in U.S. Pat. No. 5,517,571 entitled, "Active noise attenuating device of the adaptive control type" by S. Saruta & Y. Sekiguchi, and also in U.S. Pat. No. 5,448,645 entitled, "Active fan blade noise cancellation system" by J. R. Guerci. Each of these sound cancellation methods, however, is incapable of rapidly and economically analyzing and canceling out the undesirable sounds to the degree needed, especially for rapidly changing (e.g., chaotic) sounds.

In practice, obtaining accurate mathematical functions of complex sound systems is currently very difficult. Prior art excitation transducers are not accurate or fast enough and prior art algorithms are restricted to using LPC methods. Furthermore, digital processors are too slow and expensive to handle needed information, and required memories are costly. As a result, automating sound analysis so that a wide variation in sound inputs can be automatically analyzed and stored in memory for subsequent synthesis, especially in "real time," is very difficult, if not impossible in some cases. There is a need in the art for more accurate systems, for faster systems, and methods for more accurately characterizing, synthesizing, and/or canceling out acoustic signals from sound sources.

In response to the concerns discussed above, what is needed is a system and method for characterizing, synthesizing, and/or canceling out acoustic signals from sound sources that overcomes the problems of the prior art.

SUMMARY OF THE INVENTION

The present invention is a system and method for characterizing, simulating, and/or canceling out acoustic signals from sound sources. These may be applied to inanimate sound sources and animate sound sources such as the human voice. An embodiment of the invention provides a system for characterizing a sound source includes the steps of generating a numerical excitation function from excitations of the inanimate sound source; generating a numerical acoustic function from acoustic emissions of the inanimate sound source; and deconvolving the excitation function from the acoustic function to generate a transfer function which characterizes the inanimate sound source. An embodiment of the invention provides a system for synthesizing acoustic signals representing an inanimate sound source includes the steps of: receiving synthesis instructions; retrieving an excitation function from a memory based on the synthesis instructions; retrieving a transfer function from the memory based on the synthesis instructions; and convolving the excitation function with the transfer function to synthesize an acoustic signal. An embodiment of the invention provides a system for canceling out acoustic signals from an inanimate sound source includes the steps of: instantly generating an excitation function from excitations of the inanimate sound source; instantly generating an acoustic function from acoustic emissions of the inanimate sound source; calculating and storing in memory a transfer function from the excitation function and the acoustic function; receiving cancellation instructions; convolving the excitation function with the stored transfer function to synthesize a canceling acoustic signal; and broadcasting the canceling acoustic signal proximate to the acoustic emissions and fast enough to effect cancellation.

An embodiment of the invention provides a system for characterizing acoustic signals from a sound source, includes an electromagnetic (EM) sensor for monitoring excitations from the sound source; an acoustic sensor for monitoring acoustic emissions from the inanimate sound source; an EM processor for converting the excitations into an excitation function; an acoustic processor for converting the acoustic emissions into an acoustic function; a transfer function processor for generating a transfer function from the excitation function and the acoustic function. Additional EM sensors may be used to monitor secondary excitations and for generating additional transfer functions which characterize the sound source.

An embodiment of the invention provides a system for synthesizing acoustic signals from a sound source, including a memory containing an excitation function and a transfer function; a synthesis control unit for generating synthesis instructions; and a synthesis processor for retrieving the excitation function and the transfer function, and convolving the excitation function with the transfer function to synthesize an acoustic signal.

An embodiment of the invention provides a system for canceling out acoustic signals from a sound source, including an electromagnetic processor for instantly generating an excitation function from excitations of the inanimate sound source; an acoustic processor for instantly generating an acoustic function from acoustic emissions of the inanimate sound source; a transfer function processor for calculating and storing a transfer function from the excitation function and the acoustic function; a synthesis processor for receiving cancellation instructions, and for convolving the excitation function with the stored transfer function to synthesize a canceling acoustic signal; and a broadcasting unit for broadcasting the canceling acoustic signal proximate to the acoustic emissions. Animate sounds, such as human speech, can also be analyzed and synthesized using the systems and methods herein.

While the present invention is particularly applicable to repetitive and well-defined excitation sources, such as musical instruments or the human voice, non-periodic excitation sources, such as windowpanes, automobile road noise, air duct noise can also be analyzed, synthesized, or canceled out when modeled as including one or more excitation sources. Important applications of the present invention include noise cancellation in rooms or automobiles, and chaotic sound generation such as is typical of rattles, and drum snares. The present invention also finds application to musical and voice synthesizers, sound effects generators, and video and movie sound synchronization.

These and other aspects of the invention will be recognized by those skilled in the art upon review of the detailed description, drawings, and claims set forth below.

BRIEF DESCRIPTION OF THE DRAWINGS

FIG. 3 is a graph of an exemplary measured excitation function verses time;

FIG. 4 is a graph of an exemplary measured acoustic function verses time;

FIG. 9A is a graph of an exemplary measured acoustic signal;

FIG. 9B is a graph of an exemplary synthesized acoustic signal, corresponding to the exemplary measured acoustic signal.

DETAILED DESCRIPTION OF THE PREFERRED EMBODIMENT

The present invention describes a system and method for analyzing and synthesizing sounds. Using the techniques described herein, musical instruments may be more accurately simulated, sound from undesirable noise sources may be canceled, and new and unusual sounds may be generated. Animate sounds, such as human speech, are also be analyzed and synthesized using the systems and methods herein.

U.S. Pat. No. 5,729,694, entitled "Speech Coding, Reconstruction and Recognition Using Acoustics and Electromagnetic Waves" by Holzrichter and Ng, filed Feb. 6, 1996, is herein incorporated by reference and describes procedures for sound analysis and simulation based upon measuring excitations and acoustic signals from animate systems (e.g., humans) using ElectroMagnetic (EM) sensors and acoustic sensors. U.S. Pat. No. 5,729,694 also describes how simple mathematical functions, such as polynomials, sines or cosines, can model excitation sources, and how "all-pole" methods, such as Linear Prediction Coding (LPC) can be used. Most importantly, these methods describe how more accurate "pole-zero" methods are enabled by the EM sensor and acoustic sensor combination. These methods, such as Autoregressive Moving Average (ARMA), can model transfer functions with "zeros" at particular frequencies that occur in most acoustic systems. Also, incorporated by reference are the general methods of low power electromagnetic (EM) sensor design for inanimate and animate system motion measurements described in U.S. Pat. Nos. 5,345,471, 5,361,070, 5,573,012, 5,682,164, and 5,805,110 each by T. E. McEwan. The terms "EM sensor" and radar generally mean the same thing, and the term "EM waves" means EM waves that are used to measure targeted objects in the near field, intermediate field, or far field of the antenna/EM sensor system.

Figure 1:
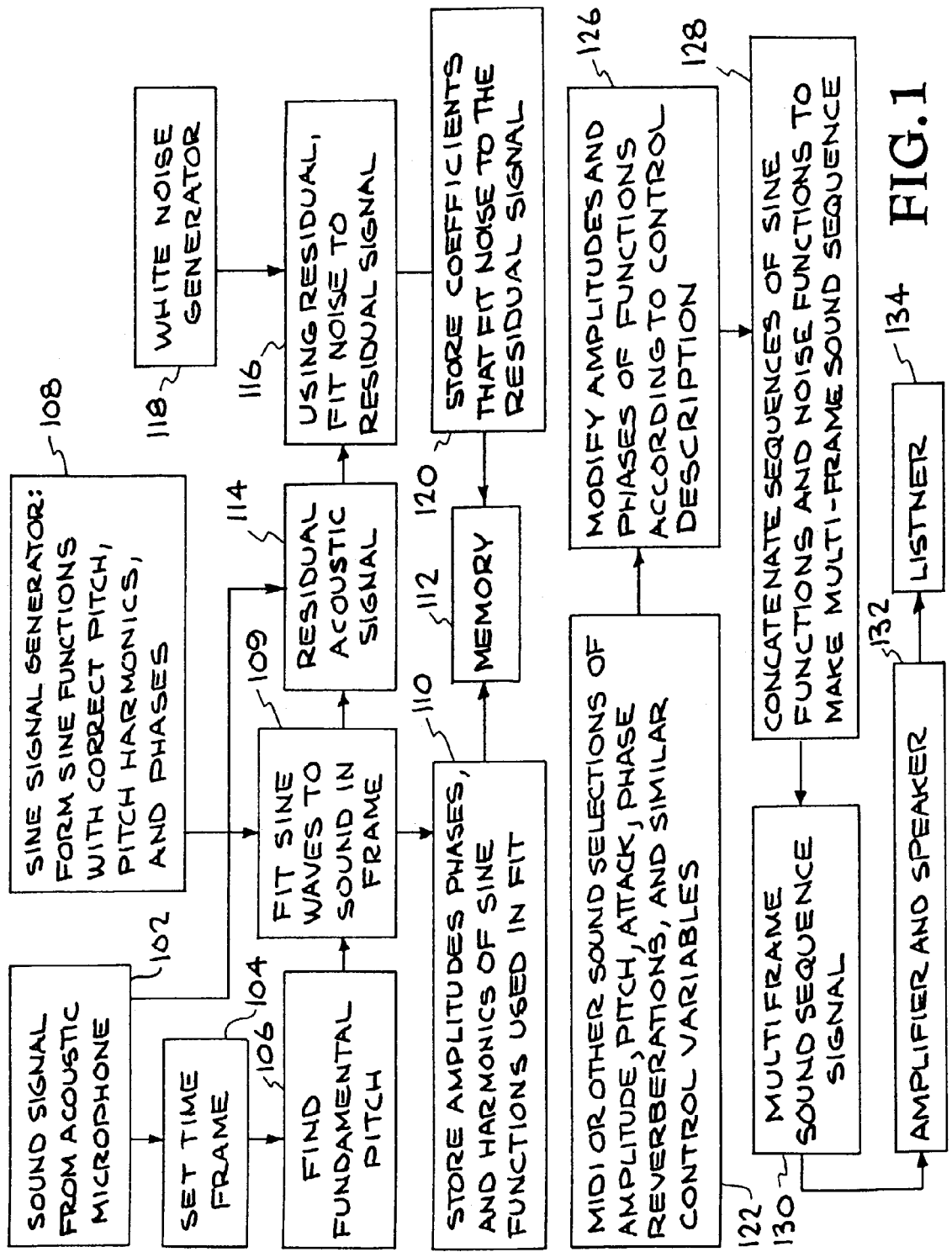
FIG. 1 is a dataflow diagram of a prior art sound synthesis system.
Figure 2:
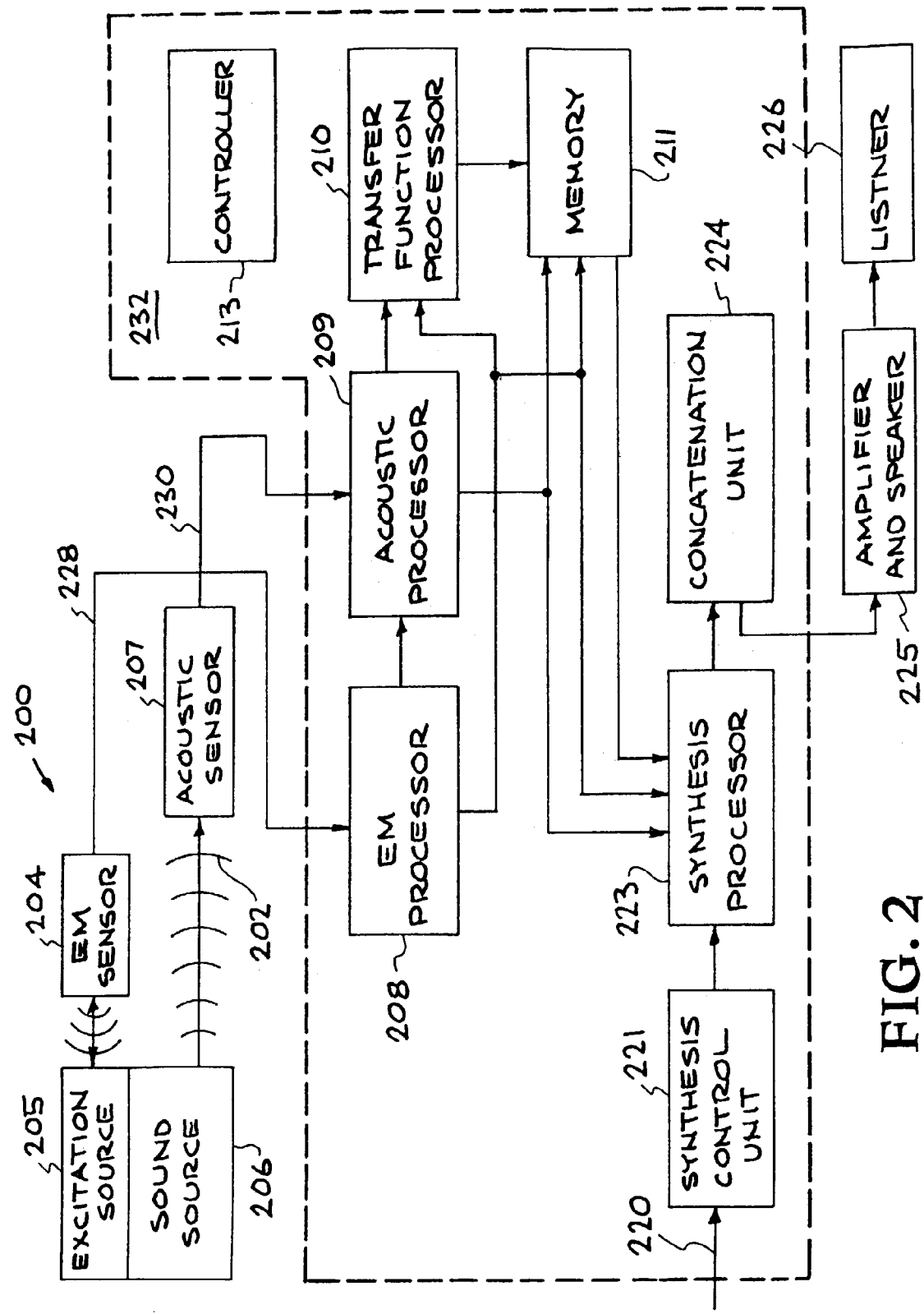
FIG. 2 is a dataflow diagram of a system for characterizing, simulating, and/or canceling out acoustic signals from sound sources.

FIG. 2 is a dataflow diagram of a system 200 for characterizing, simulating, and/or canceling out acoustic signals from inanimate sound sources. The system 200 is responsive to an inanimate sound source 206, such as a musical instrument, a noisy air-duct, or any other non-human noise source. The sound source 206 has an excitation source 205, such as vibrating strings on a guitar, and the sound source 206 radiates acoustic waves 202 in response to stimulation of the excitation source 205.

An EM sensor 204, such as that discussed in the McEwan references, generates an EM wave that reflects off of the excitation source 205 and back to the EM sensor 204. In some cases, a vibration stimulation (not shown) may be required to stimulate the excitation source 205 or serve as a primary excitation. In other cases, the excitation source 205 may represent an original excitation of the system 200, but is a separate entity. In response, the EM sensor 204 generates and transmits an EM signal over line 228 to an EM processor 208 in a computer 232. The EM sensor 204 responds to displacements of the excitation source 205. However, due to imperfections or an internal filter in the EM sensor 204, the EM signal can contain distortions. Linear distortions in the EM signal can be corrected using well known inverse filtering correction techniques. Non-linear distortions in the EM signal, or from the source can be compensated for by describing the EM signal using calibration data previously obtained.

The EM sensor 204 will respond substantially in a linear manner to excitation source 205 vibrations if the vibrations are much smaller than wavelengths of the EM sensor 204. For best results, the EM sensor should detect reflected EM waves in a linear amplitude-versus-position phase of the reflected wave's cycle. Preferably, several EM waves are transmitted in a pulse train that is detected in a coherent, homodyne detection mode by the EM sensor. The EM sensor preferably generates two signals, a normal (i) and quadrative (q) signal, which can be combined using well known methods to describe the excitation source in a linear manner.

A volume of space from which reflected EM waves can be sensed can also be limited-by range gates on the EM sensor receiver. EM waves can penetrate many types of obscuring objects to reach a volume of space where an excitation source is located. Antennas on the EM sensor can be chosen to radiate and receive energy with a divergence angle that focuses on the excitation source but avoids illuminating other incidental moving objects. As a result, the EM sensor 204 can be designed to be highly directional, and thus, for instance, pick out individual musical instrument excitations in an orchestra or to detect string vibrations on an individual instrument separate from body vibrations. Electronic filters can be used to eliminate motion sources (e.g., such as finger motion) not associated with the desired acoustic signal (e.g., string induced body-to-air vibrations). Extended spatial measurement capabilities of the EM sensor enables acquisition of many vibrational modes of the sound source, which accurately characterizes such extended excitation sources. Conversely, EM sensors and their antennas can be designed to operate in the near field, non-radiating mode. In this case, the antenna is placed very close to the targeted excitation source, usually less than one wavelength, and specific target excitation properties are obtained as a consequence of the close coupling of the antenna and excitation.

The EM sensor 204 can be pre-calibrated so that the EM signal can be converted to a fluid pressure, volume fluid flow, or mechanical vibration equivalent signal using a mathematical or numerical model.

For complex sound systems having several excitation sources, such as each string on a piano, one or more near field, intermediate field, and/or far field, EM sensors 204 can be positioned with respect to each excitation source 205 so that the sources can be monitored simultaneously. For example, four EM wave sensors can be used to measure vibrations on each wheel of an automobile suspension, in preparation for canceling out road noise transmitted into a car passenger compartment. In addition, more than one EM sensor may be used to measure multiple modes of a single excitation source.

An acoustic sensor 207 positioned at a location chosen by a user, receives the radiated acoustic waves 202 from the sound source 206 and, in response, generates and transmits an acoustic signal over line 230 to an acoustic processor 209 in the computer 232. The computer 232 is preferably of a conventional type. The computer system includes an internal memory 211 for storing computer program instructions which control how a processing unit (rendered in hardware or software) within the computer 232 accesses, transforms and outputs data. The internal memory includes both a volatile and a non-volatile portion. Those skilled in the art will recognize that the internal memory could be supplemented with computer usable storage media, such as a compact disk, a magnetic drive, or a dynamic random access memory.

A controller 213, within the computer 232, receives inputs from a variety of sources such as a Musical Instrument Digital Interface (MIDI), acoustic sensors, user interfaces, and computer sound generation systems. These inputs provide the system with information about the sound source 206. This information may include sound source types, amplitude information, and musical notes.

During analysis of the sound source 206, vibration of the excitation source 205 is either already occurring or needs to be induced, using some sort of vibration-inducing device (not shown). Preferably, all appropriate modes of the sound source 206 are stimulated. For instance, all strings of a guitar can be plucked one at a time by hand. The onset of the pluck, a "ringing" after plucking, and long time reverberations (i.e., ring-down) are recorded as needed. Multiple strings may be played at the same time and strings may be plucked at several amplitudes (i.e., volume levels) to obtain any excitation transfer function couplings, excitation couplings, nonlinear couplings, and acoustic responses. Similarly, all keys on a clarinet, or valves on a trumpet, may be pressed to change their transfer functions. For a piano, all keys are played, and different pedal positions are used to permit analysis of the excitations and corresponding sound output damping.

In some cases, sounds may be automatically identified by associating a pitch value or a pitch duration with a sound symbol such as a musical note. Such a feature of the present invention can be valuable for musicians who spontaneously create music and wish to have a musical score of their spontaneous composition. Alternatively, sound elements detected during analysis phases can be identified in response to sound identifying symbols entered into the controller 213 by a user.

The EM processor 208, within the computer 232, receives and converts the EM signal into a "measured excitation function." The measured excitation function is a set of data points that can be described in either a time domain e(t) or a frequency domain (e.g., Fourier) E($\omega$) format as a numerical sequence of numbers. FIG. 3 is a graph of an exemplary measured excitation function 300 verses time (t).

Since the numerical sequence of numbers, making up the measured excitation function, may be in the thousands, the EM processor 208 may generate a "parameterized excitation function," in order to simplify later sound synthesis operations. Alternatively, the numerical sequence itself can be kept to directly describe the measured excitation function. As a first preparatory step before generating the parameterized excitation function, the EM processor 208 parses the measured excitation function into a series of pitch periods. The pitch period represents an interval during which the measured excitation function substantially repeats itself. If the measured excitation function is periodic, previously described EM sensor time domain or frequency domain techniques are particularly easy to use to calculate the pitch period. A pitch algorithm, such as that described in the Holzrichter and Ng references, detects zero-crossings (e.g., positive-to-negative crossings) of the measured excitation function and sets the pitch period equal to a time period between two sequential zero-crossings. Alternatively, the pitch algorithm could detect other measured excitation function features, such as peak values for setting the pitch period. FIG. 3 shows an exemplary pitch period 302 and zero-crossings 304. If the measured excitation function is not periodic, such as a vibrating window or chaotic rattles from drum snares, the controller 213 requests a default time period to use from a user.

As the measured excitation function varies with time, such as when excitation of one string on a violin stops and excitation of another begins, new pitch periods may need to be calculated. The EM processor 208 calculates a new pitch period using an automated algorithm that senses a pitch charge exceeding a predetermined threshold, then institutes a new analysis phase. Alternatively, a user may input a new instruction, which identifies the new sound being played including possible pitch change.

As a second preparatory step before generating the parameterized excitation function, the EM processor 208 inverts the pitch period (in seconds/cycle) to obtain a "pitch value" in Hertz. (cycles/second) The pitch value is then associated with a sound symbol, such as a note on a musical instrument, using a lookup table and interpolation techniques. A length of time over which the pitch value is held constant (within predefined threshold limits) is used to generate identification symbols describing a time of sound duration, corresponding to musical whole, half, or quarter notes, and/or other notations. Similarly, musical-measures can also be automatically defined and noted. In some applications of the present invention, the pitch value can be displayed to a user to apprise the user of tone accuracy and quality, even if the user were playing in a high noise environment such as an orchestra.

As a third preparatory step before generating the parameterized excitation function, a "time frame" is defined. The time frame, within the measured excitation function, is here defined as a number of pitch periods over which the pitch value and/or one of the other aforementioned sound source 206 characteristics remain substantially constant. Substantially means within a set of predefined error limits. FIG. 3 shows a first exemplary time frame 306 defined by the zero-crossings 304, and an alternative exemplary time frame 308 defined by peak values 310. A typical time frame consists of about 1000 to 10,000 of the numerical sequence of numbers making up the measured excitation function.

A fourth preparatory step employs a linear or non-linear excitation source conversion function which translates "linear" measurements of an EM sensor into either a linear or non-linear function which more accurately characterizes a selected excitation of the sound source 206.

After the EM processor 208 completes the four preparatory steps, the parameterized excitation function is generated. The parameterized excitation function consists of one or more sets of mathematical equations which "best-fit" the measured excitation function data over the time frame. Best fit is here defined as selecting at least one mathematical equation and corresponding set of coefficients which together match the measured excitation function to a predetermined accuracy. The EM processor 208 uses pattern matching to identify a mathematical function, stored within the memory 211 in a mathematical database, which best fits the numerical sequence of real numbers making up the measured excitation function. Alternatively, the processor 208 uses a preselected function from the user. The mathematical database contains polynomials (e.g., Taylor series, LPC, and ARMA functions), harmonic functions (e.g., sines, cosines), piece-wise continuous functions (e.g., triangles), impulses, wavelets, and other similar basis functions. The fitting process employs fitting techniques such as least squares techniques, to obtain a set of parameter values (i.e., coefficients), which fit the parameterized excitation function to the measured excitation function. Alternatively, all (or a subset) digital signal values from the A/D converter (e.g. the numerical sequence of real numbers making up the measured excitation function) can be stored and then used as the parameterized excitation function, where the parameters are the numerical sequence of numbers.

For each time frame, the pitch periods, pitch values, musical notes, parameterized excitation function, function coefficients, and other identifying information are stored in the memory 211 as an "excitation feature vector." A different excitation feature vector is calculated as needed during analysis of the sound source, for each of the time frames making up the numerical sequence of numbers making up the measured excitation function.

The acoustic processor 209, within the computer 232, receives the acoustic signal, performs analog to digital (A/D) conversion and amplitude correction, and generates a measured acoustic function. The measured acoustic function may be described in either a time domain a(t) or a frequency domain A($\omega$) format, and it can be parameterized or compressed. FIG. 4 is a graph of an exemplary measured acoustic function 402 verses time (t). In an alternate embodiment, a second acoustic sensor simultaneously measures acoustic information appropriate to a second channel of an acoustic signal from the sound source 206 so as to obtain a stereo effect.

The acoustic processor 209 time-correlates the measured acoustic function with the measured excitation function. Time-correlation between these two functions is required since any activity by the excitation source 205 is quickly sensed by the EM sensor 204, while in contrast the acoustic sensor 207 records a corresponding acoustic signal only after vibrations from the excitation source 205 travel through the sound source 206, then through the air surrounding the sound source 206 to the acoustic sensor 207. A time delay results since the EM waves reflecting off the excitation source 205 travel at the speed-of-light, while the acoustic waves emanating from the sound source 206 travel only at the speed-of-sound. Time-correlation is performed by calculating a time delay between the measured excitation function and the measured acoustic function.

The time delay can be obtained by at least one of three methods. First, the acoustic processor 209 can compare a time-of-onset of the measured excitation function with a time-of-onset of the measured acoustic function.

Second, the acoustic processor 209 can accept a specified time delay in response to a user input received by the controller 213. The user would determine the time delay by measuring a distance (d1) between the EM sensor 204 and the excitation source 205 and a distance (d2) between the sound source 206 and the acoustic sensor 207. Divide d1 by the speed of light and d2 by the speed of sound and subtract to obtain the delay time. The second method is preferably used when there are no important, long-duration multipath sound reverberations in the sound source 206.

In the third method, the time delay can be obtained from a phase delay forming a part of a transfer function relating the excitation source 206 to the acoustic output 207 (calculation of this transfer function is described below). The measured acoustic function, the time delay, and any other related information is then stored as an "acoustic feature vector" in memory 211 and used as needed.

There are two special cases of interest that affect what information is stored in the excitation feature vector and the acoustic feature vector. First, when a vibration causes the sound source 206 to reverberate resulting in a measured acoustic function that lasts much longer than a duration of the measured excitation function, a large amount of memory and processing will be consumed unless the measured data is compressed. If the reverberation is a decaying cyclic wave, a first few cycles can be analyzed as above, and then a damping function and decay rate d (e.g. $\exp(-dt)$), and a time of repetition may be algorithmically determined using standard waveform analysis techniques and stored in the feature vector. In a second case, when both the measured excitation and acoustic functions reverberate for an extended period of time and the time delay between two successive sets of measured excitation and acoustic functions remain relatively constant, the EM processor 208 generates information on the damping function and decay rate (d), which defines a decay rate for both of the measured functions. The extra information is then added to both of the feature vectors.

A transfer function processor 210 receives the parameterized excitation function and the measured acoustic function. The transfer function processor 210 calculates either a transfer function or a digital filter function for the sound source 206. The transfer function and digital filter function can either be numerically represented or parameterized. Parameterization reduces an amount of data used during subsequent calculations. For instance, a numerically represented transfer function may contain about 2000 numbers (i.e., 1000 complex numbers from a 1000 point numerical Fourier transform), while a parameterized transfer function may contain only about 65 complex numbers (i.e., 58-poles, and 7-zeros).

By having continuous excitation information using the EM sensor(s), either standard functions using "poles" (e.g., LPC analysis) or more complex functionals using both "poles" and "zeros" can be used to calculate the transfer function. More complex transfer functions (and the related digital filter function) mathematically represent, to a higher degree of fidelity than prior art techniques, how the sound source 206 transforms vibrations from the excitation source 205 into the radiated acoustic waves 202. This process of calculating the transfer function "matches" the parameterized excitation function, via a "deconvolving" process, to the measured acoustic signal. Small errors in the parameterized excitation function are accommodated and corrected by the transfer function. Parameters of the transfer function are selected by well-known algorithms to best transfer the parameterized excitation function to the measured acoustic signal.

A filter representation of the sound source 206 is preferred in cases where the measured excitation function varies rapidly with respect to time while the transfer function remains relatively constant. Sound sources 206 such as building structures and musical string instruments are two examples of such sound sources.

A transfer function representation of the sound source 206 is preferred in cases where the measured excitation function of the sound source 206 remains relatively constant while in time the transfer function varies. An example of such a sound source is a clarinet where each fingering of a key changes an effective tube length and thus the transfer function, while reed vibrations (i.e., an excitation source) remain relatively constant.

Digital filter function and transfer function coefficients can be easily interchanged (see Oppenheim reference) in the above example. In this specification, additional discussion referring to transfer functions also applies to corresponding digital filters.

Transfer functions are modeled using either LPC, ARMA, Fourier, or time domain techniques such as wavelets. However, for sound sources with "zeros" in their output spectra, the "pole-zero" or ARMA approach enabled by methods herein are especially useful and are enabled by excitation description methods herein. Fidelity of a parameterized transfer function depends upon a numbers of poles and zeros used.

Those skilled in the art will recognize that other numerical techniques, incorporating EM and acoustic sensors, may be used. In some cases, interpolation techniques may be used to minimize data storage and analysis time. A limited number of preselected excitation and transfer function conditions of the sound source 206 can be selected and analyzed with other conditions determined by interpolating between stored data. For example, in a slide trombone, relatively few slide positions would need to be measured. Gaps in the measured excitation and acoustic functions for other slide positions can then be "filled-in" by interpolating between slide positions for which actual measured data is obtained.

All of the transfer function data calculated for the sound source 206, (e.g. transfer function coefficients and additional information), are stored in the memory 211 as "transfer function feature vectors." The transfer function feature vectors may include information on the type of sound system being analyzed, types of functions used for parameterization, parameter coefficient values, coefficient changes, timing information, digital filter values, time frame connectivity, sound identification symbols, and system and memory control values.

Once calculated, the transfer function feature vectors can provide unique and valuable information about the sound source 206. For instance, a transfer function feature vector calculated for a new musical instrument and stored in memory 211 can serve as a template for testing the musical instrument when it is older. Any changes in the transfer function feature vectors over time may indicate some structural damage to the instrument.

In addition, transfer function features are associated with oscillations within substructures of a sound device. These important features of the transfer functions may be measured directly using an EM sensor to measure purposely induced, structure oscillations. These are then used to uniquely identify (i.e., fingerprint) a sound source. Priceless musical instruments or other sound sources could then be distinguished from frauds. Use of the system 200 in this way permits the user to uniquely characterize and identify any physical structure that is responsive to purposely imposed and measured vibrations, for any number of diverse identification needs.

Once the sound source 206 has been analyzed, the feature vectors stored in the memory 211 can be used to electronically generate a synthesized acoustic signal. Synthesized acoustic signals can be used to either mimic or cancel out sound source 206 acoustic signals. In addition, for unusual sound generation, non-physically realizable changes in excitation or transfer function may be implemented by the user. During synthesis, a synthesis control unit 221 accepts input from either the controller 213 or external control signals on line 220. Standardized sets of external control signals conforming to MIDI algorithms can be used to define corresponding excitations, transfer functions, residual excitation functions, pitch variations, amplitude variations, and other data used by the synthesis control unit 221. In response to these inputs, the synthesis control unit 221 selects a parameterized excitation and transfer function from the memory 211, which prescribe a type, time frame, pitch, amplitude modulation, connectivity, and quality of the synthesized acoustic signal for each time frame. Those skilled in the art will recognize that the system 200 may be used to generate a multi-instrumental synthesized acoustic signal which includes many different excitation and transfer functions, representing many different sound sources for each time frame.

In response to instructions from the synthesis control unit 221, a synthesis processor 223 accesses the parameterized excitation and transfer functions from memory 211 and constructs a synthesized acoustic signal segment, generated by convolving (or filtering) the parameterized excitation with the corresponding transfer function for each time frame. Additional details are later provided with reference to FIG. 8.

A concatenation unit 224 connects the synthesized signal segment to any previous synthesized acoustic signal segment from a previous time frame or frames. It responds to a predetermined pattern designated by the controller 213 to create a continuous multitime frame synthesized acoustic signal. The synthesized acoustic signal is then sent to the amplifier/speaker 225 for digital to analog (D/A) conversion and broadcasting to a listener 226.

If the system 200 is used for sound cancellation, the system 200 must analyze the sound source 206 and broadcast a canceling acoustic signal faster than a time it takes the acoustic waves 202 to reach the listener 226. The near instant measurement qualities of the EM sensor 204 make this possible. To use the system 200 to cancel sound from the sound source 206, a set of transfer functions, which characterize the sound source 206, must have already been analyzed with parameterizing coefficients stored in the memory 211. The controller 213 then configures the EM processor 208 to parse "real time" the EM signal coming in on line 228 into predetermined time segments. The length of these time segments depends upon a variety of factors. A most important factor is how close the listener 226 is to the sound source 206. For example, if the listener 226 is about 10 feet from the sound source 206, the time segments might be chosen to be 5 msec or less, corresponding to about 5 feet or less of sound travel. The EM processor 208 then generates a set of short parameterized excitation functions, which are then sent, through the memory 211 or by direct transmission, to the synthesis processor 223.

The synthesis processor 223 accesses pre-stored parameterized transfer functions corresponding to the sound source 206 and the acoustic environment. The synthesis processor 223 then filters (or convolves) the short parameterized excitation function, with pre-stored transfer function filter coefficients corresponding to the frame rate of the EM signal, and creating a synthesized signal over a short time segment, called an intermediate signal. The synthesis processor 223 sends the short intermediate synthesized signal to the concatenation unit 224 which connects the synthesized intermediate segments of acoustic signals into a smoothly synthesized canceling acoustic signal. Concatenation procedures are well known by practitioners in the art of digital sound generation. The concatenation unit 224, also delays the signal appropriately, inverts the synthesized acoustic signal in sign, and sends the synthesized acoustic signal to the amplifiers and speaker 225. Because of the time of travel of the sound, the processors typically have less than 5 ms to process and broadcast a canceling sound.

The amplifiers and speaker 225 broadcast the inverted synthesized acoustic signal to the listener 226. Upon broadcasting the inverted synthesized acoustic signal, the acoustic waves 202 radiating from the "undesirable" sound source 206 are canceled out. Best results are achieved when the acoustic sensor 207, used to analyze the system transfer functions and to sense needed corrections, is located as close as possible to a predetermined sound cancellation point, such as the listener 226. The synthesis processor 223 may use additional information received from the acoustic sensor 207 and its processor 209 to adjust the amplitude, phase, and filter coefficients of the system transfer function using processor 210, and output acoustic signal levels and delays using processors 223 and 224, so as to minimize sound pressure levels near the listener 226.

FIGS. 5A through 5E depict some exemplary positions for an EM sensor and an acoustic sensor with respect to a sound source. The sensors preferably are positioned based on the following factors. EM waves from the EM sensor should be able to pass through objects, which obscure the excitation source. The EM sensor should be positioned and filtered so as not to measure other moving or parasitic vibrating bodies nearby. The EM sensor and acoustic sensor should not interfere with normal operation of the excitation source. A variety of EM sensors can be positioned in a near, intermediate, or far field position with respect to the excitation source and in a radiating or non-radiating mode. Acoustic sensors are preferably positioned to receive radiated acoustic waves so that a desired spatial acoustic pattern is recorded. This pattern may depend upon environmental and user considerations, as well as effects due to a distance of the acoustic sensor from a sound source.

In order to enhance EM wave reflectivity from an excitation source (if needed), a thin reflecting pattern, that is made from vibrationally non-interfering metal, semiconductors, or a high dielectric coatings can be added to a part of the excitation source. In other cases, special types of EM reflecting targets may be placed such that they vibrate and reflect EM waves proportionally to the excitation source. For example, a thin metalized rubber membrane, which vibrates in proportion to air pressure inside the instrument, may be located on the side of a wind instrument near the mouthpiece.

Figure 5A:
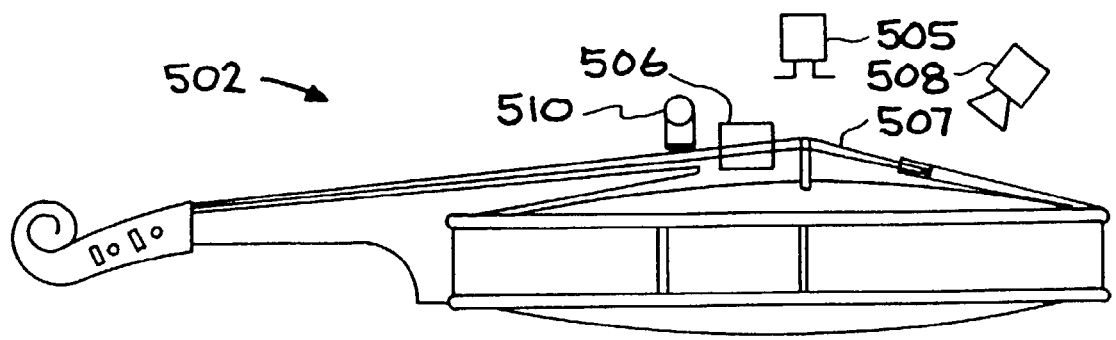
FIG. 5A is a pictorial diagram of indicating exemplary positioning for an electromagnetic sensor and an acoustic sensor for plucked or bowed string instruments, such as a guitar.

FIG. 5A is a pictorial diagram of indicating exemplary positioning for an electromagnetic sensor and an acoustic sensor for plucked or bowed string instruments, such as a guitar or a violin 502. In this figure, a first EM sensor 505 is placed over a first portion of the violin 502 strings near a bridge. If desired, a second EM sensor 506 may be placed over a second portion of the violin 502 strings, for example, to measure perpendicular motions of the string. An acoustic sensor 508 is pointed toward the violin 502. To enhance EM reflections, metalization may be added to portions of the violin strings if they are not already metal strings.

Figure 5B:
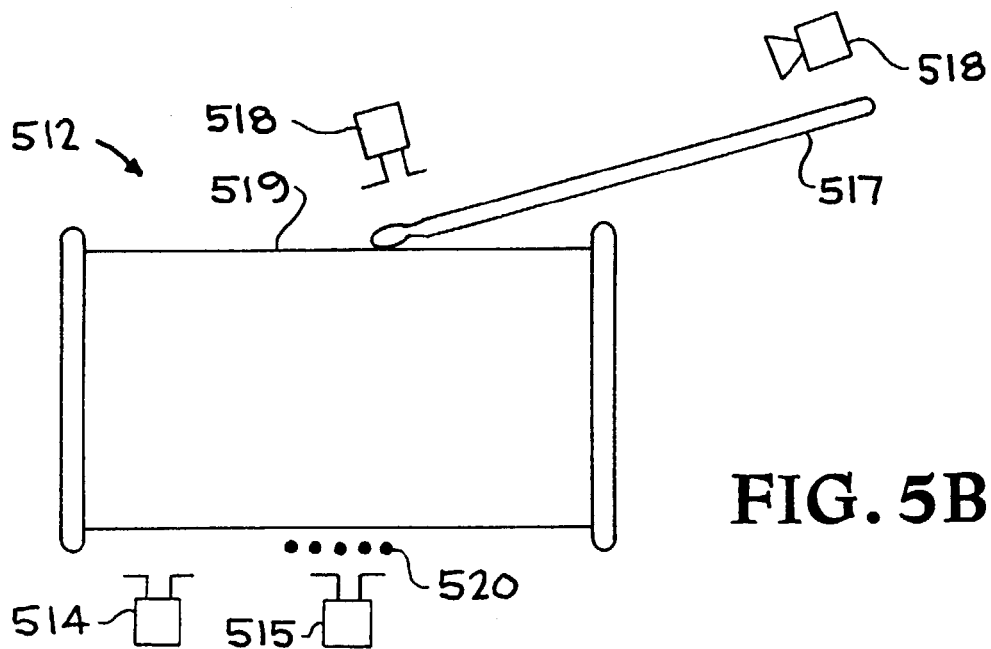
FIG. 5B is a pictorial diagram of indicating exemplary positioning for electromagnetic sensors and the acoustic sensor for a percussion instrument, such as a drum.

FIG. 5B is a pictorial diagram of indicating exemplary positioning for electromagnetic sensors and the acoustic sensor for a percussion instrument, such as a snare drum 512. In this figure, a first EM sensor 514 is placed under the drum 512 with its range setting adjusted to measure the drum head motion. A second EM sensor 515 may be placed under a set of snares on the drum 512, and a third EM sensor 516 may be placed proximate to where a stick 517 hits the drum 512, and an acoustic sensor 518 is pointed facing the drum 512. Such multiple EM sensors may be desirable to use since the drum 512 has multiple excitation sources, which can be analyzed. For instance, the snares on a snare drum respond separately (as a secondary excitation) from impulsive excitation of a drumhead 519 being hit by the stick 517. A thin reflecting film can be applied to drum heads 519 and other portions of the drum 512 to enhance EM reflectivity.

Timing events, caused by "indirect" excitation of the drum 512, or other instruments, can also be analyzed. For instance, timing impact of the drumstick 517 on the drumhead 519 can also be characterized. EM sensors can monitor such indirect excitations when the EM sensor is adjusted to have a low enough frequency response to capture the relatively slow motions. This technique can also be used to monitor onset of bow motions on a violin for string contact, and piano string hammer motions. This information can then provide useful timing information so the system 200 can automatically prepare itself to respond to an impulse, or onset of other excitations.

Figure 5E:
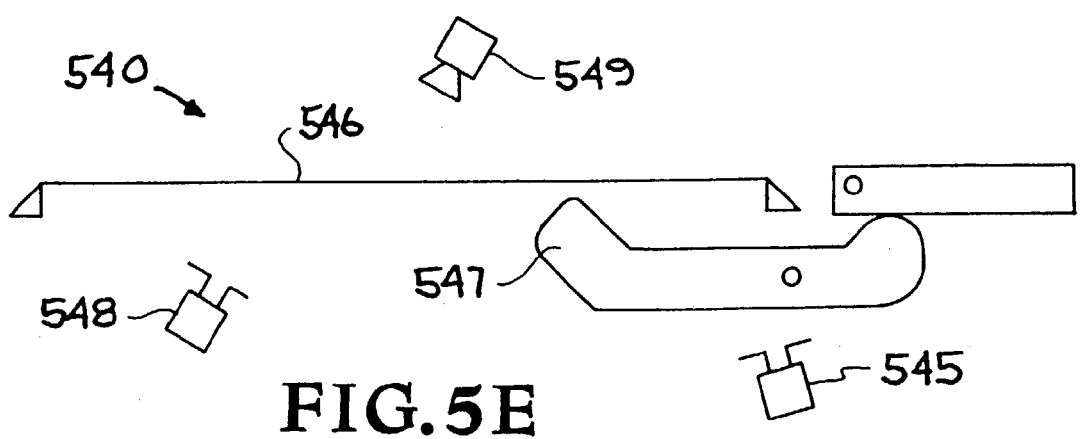
FIG. 5E is a pictorial diagram of indicating exemplary positioning for electromagnetic sensors and the acoustic sensor for a hammered-string instrument, such as a piano.
Figure 5C:
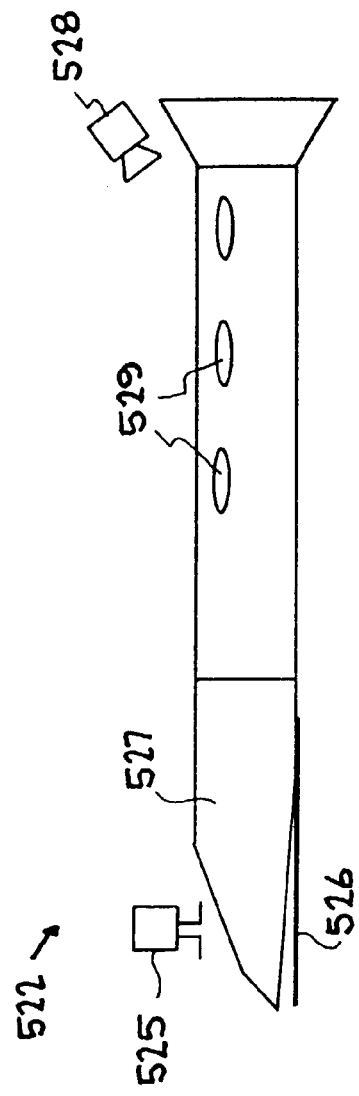
FIG. 5C is a pictorial diagram of indicating exemplary positioning for an electromagnetic sensor and the acoustic sensor for a woodwind musical instrument.

FIG. 5C is a pictorial diagram of indicating exemplary positioning for an electromagnetic sensor and the acoustic sensor for a woodwind musical instrument 522. In this case, a reed 526 is an excitation source so that an EM sensor 525 is placed proximate to the reed 526. EM waves from the EM sensor 525 pass through a mouthpiece 527 and through the lips (not shown), reflecting off the reed-air 526 and reed-lip interface. EM reflectivity may be enhanced by affixing a thin layer of metal on either an inside or outside surface of the reed 526.

Figure 5D:
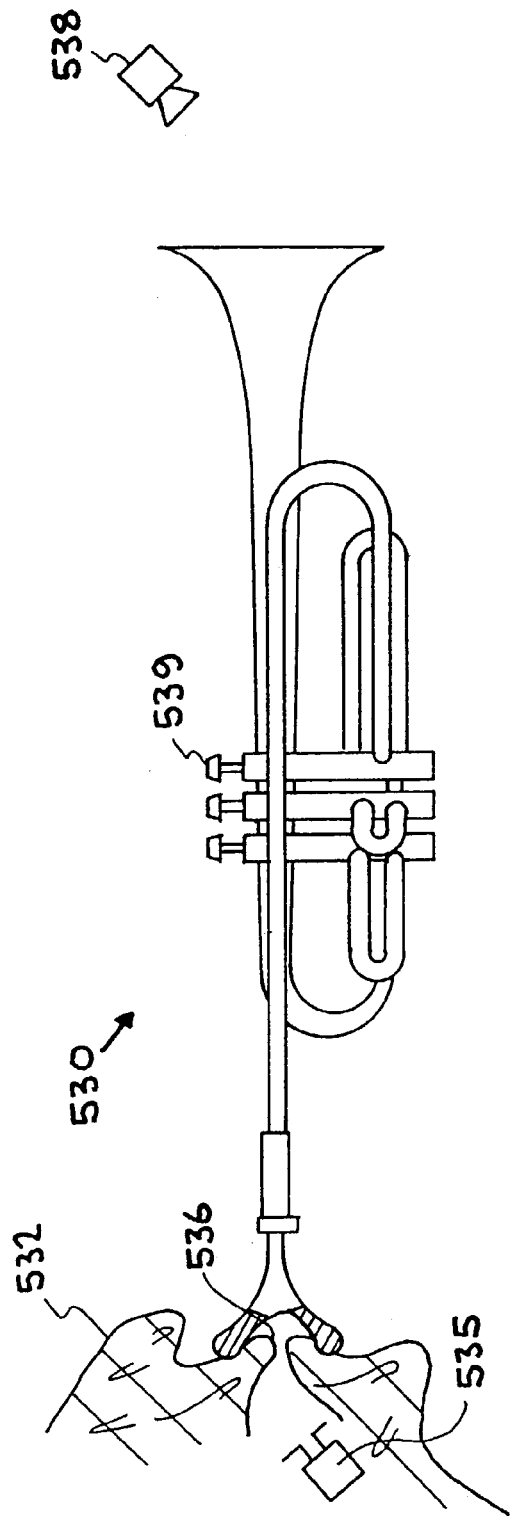
FIG. 5D is a pictorial diagram of indicating exemplary positioning for an electromagnetic sensor and the acoustic sensor for a brass musical instrument, such as a trumpet.

FIG. 5D is a pictorial diagram of indicating exemplary positioning for an electromagnetic sensor and the acoustic sensor for a brass musical instrument, such as a trumpet 530. In this figure, a first EM sensor 535 is placed near a cheek of a player 532, and an acoustic sensor 538 is pointed facing the trumpet 530. Measuring air excitations directly in the trumpet 530 is difficult. As a result, an auxiliary excitation source, vibrating lips 536 in this case, is monitored with the EM sensor 535. Linear lip 536 vibrations thus can be used to generate a measured excitation function which can then be transformed to an airflow excitation function for use within the trumpet 530, using known air-flow or air-pressure versus area functions (e.g., an airflow excitation function can be determined by converting measured linear excitation source signals to a change in lip-aperture area.) Similarly an EM sensor may measure skin motion on the head or neck of a speaker or it may measure internal vocal tract wall movements which may be used to estimate a voiced excitation function caused by vocal fold opening and closing. Alternatively, empirical functions to transform EM sensor data to excitation functions can be obtained by trial and error analysis to give the best description of the sound source. Another sound source, which may benefit from this auxiliary excitation source technique is a rotational machinery noise transmitted through air conditioning ducts into a room. By using EM sensors to measure pulsations of a duct surface that represent an auxiliary excitation source, an internal duct air pressure excitation function can be derived by transforming duct motion to internal air pressure.

For a difficult-to-access excitation source, such as, vibrating lips in a trumpet, preferably either a glass or other EM wave-transmitting mouthpiece is used. Experiments have also shown that a 12-cm EM wave easily measures lip vibrations on the metallic trumpet mouthpiece; however, as shown below a 7-cm wave would be better. If the trumpet 530 has a metallic mouthpiece, the EM sensor 535 can be optimized so that its waves can reach the vibrating lips 536, by selecting an EM wavelength, which matches transverse dimensions of the mouthpiece. More specifically, the dielectric constant, $\omega_{tissue}$, of the lips 536 pressed against the metallic mouthpiece, determines a local dimension, $1_{mouthpiece}$ which an EM wave must match for a good measurement. The corresponding wave dimension in air becomes:

$$1_{air} = 1_{mouthpiece} \times (\omega_{tissue})^{1/2}$$

for typical conditions. For a $\omega_{tissue}$ of about 50, and a metallic mouthpiece of dimension, $1_{mouthpiece}$ of about 1.0 cm, the corresponding wavelength in air $1_{air}$ is about 7 centimeters, which corresponds to a 4-GHz EM wave.

FIG. 5E is a pictorial diagram of indicating exemplary positioning for electromagnetic sensors and the acoustic sensor for a hammered-string instrument, such as a piano 540. In this figure, an acoustic sensor 549 is placed near the piano 540, a first EM sensor 548 is placed facing the string, and a second EM sensor 545 (if needed) is placed to sense hammer 547 motion.

Figure 6:
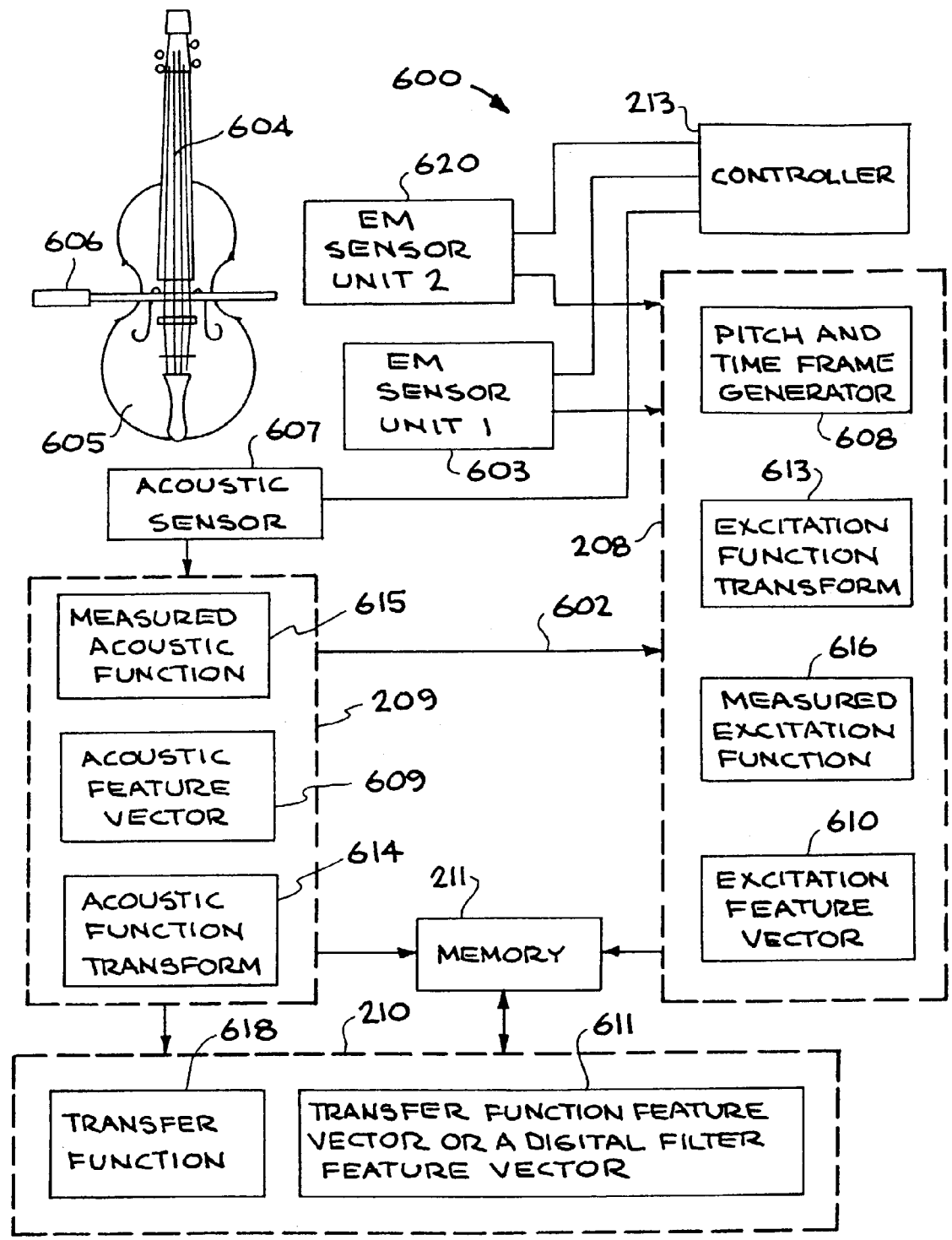
FIG. 6 is a dataflow diagram of the system as applied to a violin, for an exemplary set of conditions.

FIG. 6 is a dataflow diagram 600 of the system 200 as applied to a violin, for an exemplary set of conditions. A first EM sensor 603 measures various violin string 604 vibrations under direction of the controller 213. A second EM sensor 620 measures (if needed) either bow 606 motion or a perpendicular direction of string 604 vibration. A low frequency cutoff for the first EM sensor 603 is set to 70 Hz, so as not to detect movements of a violin bow 606, and a high cutoff frequency is set to 7-kHz, so as to capture vibrations of a set of violin strings 604. For example, the second EM sensor 620 may be adjusted to measure the string vibrations in perpendicular directions to the body. To generate excitation and acoustic signals for analysis, the set of strings 604 on the violin 605 are vibrated in response to movement of the violin bow 606. The controller 213 also controls an acoustic sensor 607, located at a predetermined distance from the violin 605.

The EM processor 208 uses the first EM sensor 603 to generate a first measured excitation function 616 or a first measured excitation transform 613, either of which may be parameterized to reduce subsequent computational complexity. A pitch and time frame processor 608, within the EM processor 208, uses either repetitive signals from the first EM sensor 603 signal, or control inputs from the controller 213 to determine a time frame for the excitation function 616 and the first transform 613. Next, the EM processor 208 generates a first excitation feature vector 610 for every time frame, which is stored in the memory 211. Data from the second EM sensor 620 can be recorded, processed, and used as needed to generate (if needed) a second measured excitation function or a second measured excitation transform, and a second excitation feature vector in a same manner as just described.

The acoustic processor 610 uses the acoustic sensor 607 signal to generate a measured acoustic function 615 or an acoustic function transform 614, either of which may be parameterized to reduce subsequent computational complexity. An acoustic feature vector 609 is calculated for each time frame and then stored in the memory 211. The transfer function processor 210 uses the excitation and acoustic feature vectors to calculate and parameterize a transfer function 618, which is then translated into a transfer function feature vector 611 and stored in the memory 211.

Figure 7A:
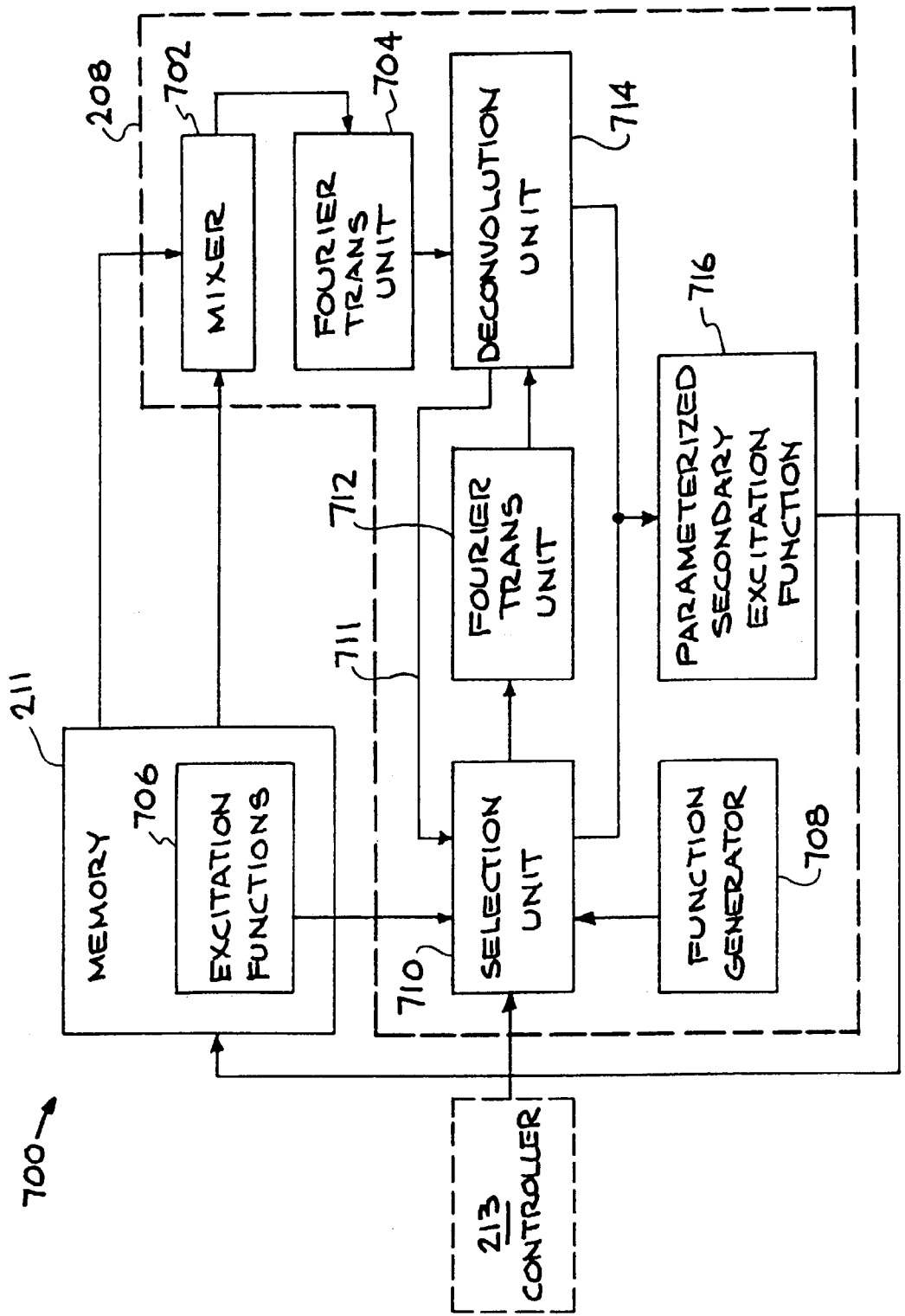
FIG. 7A is a dataflow diagram for estimating a secondary excitation function for a sound source using only one EM sensor.
Figure 7B:
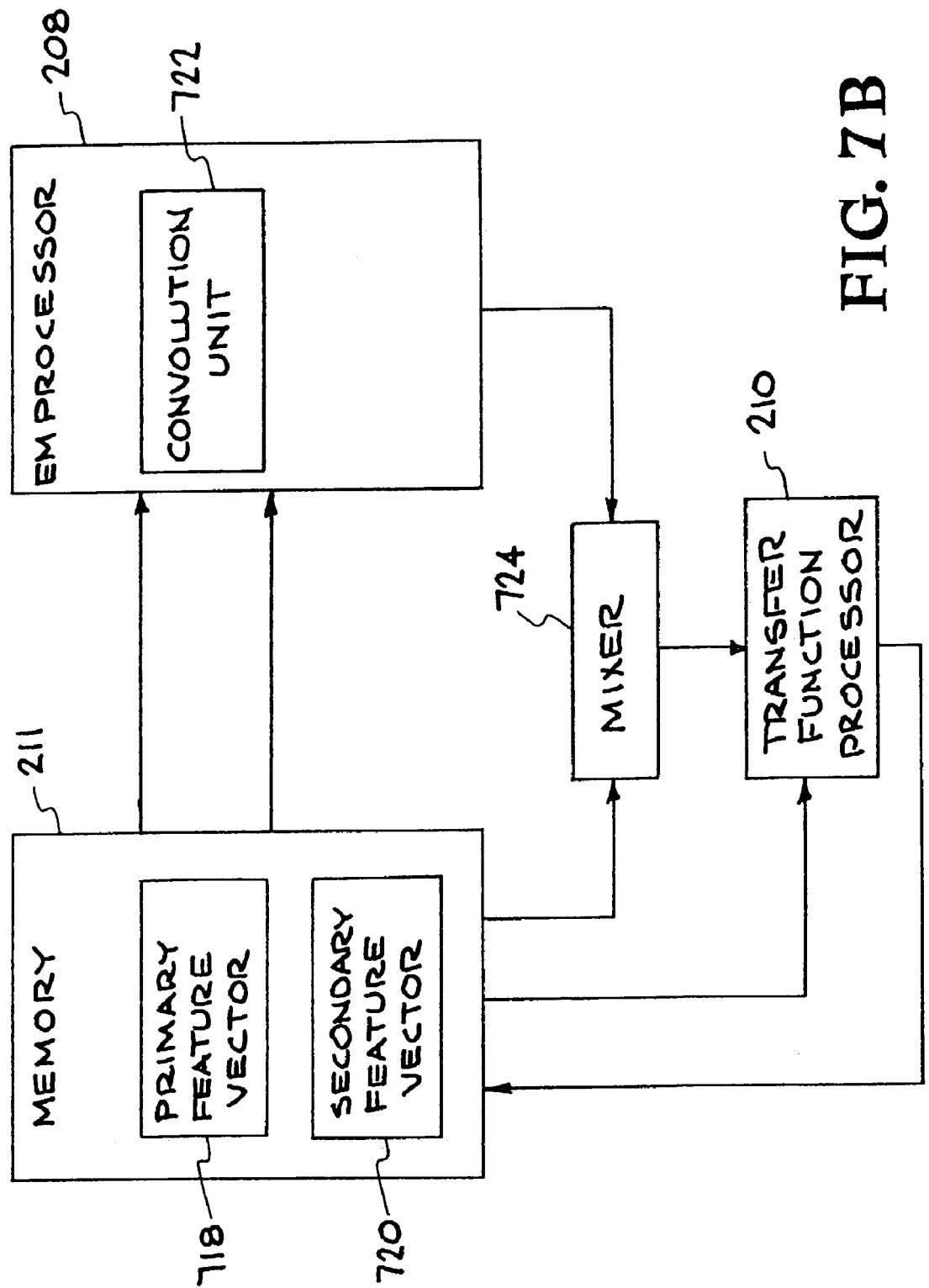
FIG. 7B is a dataflow diagram for estimating a secondary excitation function using two EM sensors.

FIGS. 7A and 7B show two different ways in which sound sources which include both primary and secondary excitations may be characterized. A third way is discussed after FIG. 7B. Primary excitations are here defined as those sound source vibrations, which lead to the greatest amount of acoustic energy. For instance, if the sound source is a violin, the greatest amount of vibration energy is generated by violin strings; or if the sound source is a snare drum, the greatest amount of vibration energy is generated as the drumstick strikes a drumhead. Because of this large amount of vibration energy, the primary excitations are easiest to analyze. Secondary excitations are here defined as those sound source vibrations that generate less acoustic energy. Thus, if the sound source is the violin, the secondary excitation could be vibrations from a violin bow itself as it moves across the violin strings, or could be finger slips on strings as a player changes a note, or the secondary excitation could be perpendicular motions of the strings. Or, if the sound source is the snare drum, the secondary excitation could be snares on the drum, vibrating chaotically in response to the drum stick beats on a drum head. In the case of the human voice, a secondary excitation can be the skin on the neck or head, or it can be the vocal tract walls that are moved by the air-pressure pulses from the primary vocal fold excitation Many excitation sources have both "periodic" and "chaotic" energy components. A periodic energy component is one in which several oscillatory cycles of excitation can be measured, while a chaotic energy component is one which is more random and resembles chaotic noise. Depending upon the sound source, the primary excitation can either be dominated by periodic energy (such as in the case of a violin), or chaotic energy (such as in the case of an air duct). Secondary excitations can either be chaotic (e.g., drum snares) or periodic (e.g., violin strings vibrating out of plane).

FIG. 7A is a dataflow diagram for generating a parameterized secondary excitation function for a sound source using only one EM sensor. This is a first approach for characterizing secondary excitations which accompany primary excitations. The EM processor 208 retrieves both a previously measured primary excitation function and a previously parameterized primary excitation function from the memory 211. A mixer 702, within the EM processor 208, subtracts the parameterized primary excitation function from the measured primary excitation function, resulting in a residual (a.k.a. an estimated secondary) excitation function. The estimated secondary excitation function can be converted into a frequency domain representation by a first Fourier transform unit 704, but this step is optional.

Under command of a deconvolution unit 714 over line 711, a selection unit 710 routes a chaotic excitation function from either a set of pre-stored excitation functions 706 stored in the memory 211, or from a function generator 708 within the EM processor 208 to the deconvolution unit 714. Preferably, the chaotic excitation functions are parameterized, however they need not be. The function generator 708 generates various chaotic excitation functions using well-known chaotic noise algorithms. A second Fourier transform unit 712 converts the chaotic excitation function into a frequency domain representation, but this step is optional.

The deconvolution unit 714 deconvolves the estimated secondary excitation function with the chaotic excitation function to produce an error function. The deconvolution unit 714 generates the error function for each chaotic excitation function received from the selection unit 710. A predetermined number of chaotic excitation functions are received, based upon various user set-up parameters. The deconvolution unit 714 selects a chaotic excitation function which results in a smallest error function. This selected chaotic excitation function becomes the parameterized secondary excitation function 716.

Alternatively, in cases where the system 200 is used in conjunction with only one or a few similar types of sound sources, the deconvolution unit 714 can be pre-programmed by the controller 213 to always select a particular chaotic excitation function as the parameterized secondary excitation function.

The parameterized secondary excitation function 716 is then stored in the memory 211 as part of the excitation feature vector. Once stored in the memory 211, the transfer function processor 210, the synthesis processor 223, and the concatenation unit 224 can access both the parameterized primary and chaotic excitation functions and simulate or cancel out a measured acoustic excitation function.

FIG. 7B is a dataflow diagram for estimating a secondary excitation function using two EM sensors. This is a second approach for characterizing secondary excitations which accompany primary excitations. In this scenario, a first and second excitation source are respectively monitored by a first and second EM sensor, and a single acoustic sensor measures all acoustic vibrations. An example of this scenario is shown by the snare drum 512, in FIG. 5B, having the first EM sensor 514 and the second EM sensor 515. Typically, the excitation sources are assigned to the EM sensors such that vibrations from the first excitation source are more periodic in nature, while vibrations from the second excitation source are more chaotic in nature. Even though vibrations from the secondary excitation source are often more chaotic in nature, such vibrations tend to have a well-defined onset, often coinciding with an onset of vibrations from the more periodic vibrations from the primary excitation source. Periodic secondary excitations may also be characterized using the method to be described.

A measured primary excitation is obtained from the first EM sensor, a measured secondary excitation is obtained from the second EM sensor, and a measured acoustic signal is obtained from the acoustic sensor, each of which is stored in the memory 211. The EM processor 208 generates parameterized primary and secondary excitation functions from the measured primary and secondary excitations respectively. The acoustic processor 209 generates a parameterized acoustic function from the measured acoustic signal. The transfer function processor 210 calculates a primary transfer function using the parameterized primary excitation function and the parameterized acoustic function. A primary time frame is calculated based on the primary excitation function, and is later used when determining a secondary time frame for measuring and parameterizing the secondary excitation function. Operation of the EM processor 208, the acoustic processor 209, and the transfer function processor 210 to effect the above calculations is discussed with reference to FIG. 2. The calculated functions and time frames are then stored accordingly in either a primary or a secondary feature vector 718 and 720 in the memory 211.

After the preparatory calculations just described are completed, a convolution unit 722, within the EM processor 208, synthesizes an estimated primary acoustic function by convolving the parameterized primary excitation function with the primary transfer function. A mixer 724 then subtracts the estimated primary acoustic function from the parameterized acoustic function to form an estimated secondary (i.e., a residual) acoustic function. The transfer function processor 210 then uses the estimated secondary acoustic function and the parameterized secondary excitation function, retrieved from the memory 211, to calculate a secondary transfer function, using the techniques described with reference to FIG. 2. The transfer function processor 210 also calculates a set of coefficients which parameterize the secondary transfer function.

The transfer function processor 210 then stores the secondary transfer function and related coefficients in the secondary feature vector 720. The synthesis processor 223 and the concatenation unit 224 can now access the primary and secondary feature vectors to synthesize various acoustic signals. The feature vectors can be used to either simulate the sound source 206 and its acoustic output, or to cancel out the acoustic signal generated by the sound source 206.

A third approach for characterizing secondary excitations accompanying primary excitations, which is a hybrid of the first and second approaches described with reference to FIGS. 7A and 7B, may also be used. In this approach an EM sensor is used to monitor a first excitation source, an acoustic sensor is used to monitor acoustic vibrations, however, a second excitation source is not monitored. Instead a preselected chaotic excitation function is used to characterize the second excitation source. A key to this approach is an assumption that even though vibrations from the second excitation source are probably more chaotic in nature, their functional form can either be estimated ahead of time by an experienced technician, characterized ahead of time, or automatically estimated using the error measurement techniques described with reference to FIG. 7A. This approach is very useful for characterizing unvoiced segments of human speech.

To begin, the EM processor 208 generates a parameterized primary excitation function from the measured primary excitation, and the convolution unit 722 synthesizes an estimated primary acoustic function by convolving the parameterized primary excitation function with the primary transfer function. The mixer 724 subtracts the estimated primary acoustic function from the parameterized acoustic function to form the estimated secondary (i.e., residual) acoustic function. Each of the above steps are performed as described with reference to FIG. 7B.

Now, instead of obtaining a parameterized secondary excitation function from the memory 211 as was done in FIG. 7B, the transfer function processor 210 retrieves a preselected excitation function from either the function generator 708 or a set of excitation functions stored in the memory 211, as was described with reference to FIG. 7A. The transfer function processor 210 now calculates the secondary transfer function and related coefficients using the estimated secondary acoustic function and the preselected excitation function in the same manner as was described with reference to FIG. 7B.

Figure 8:
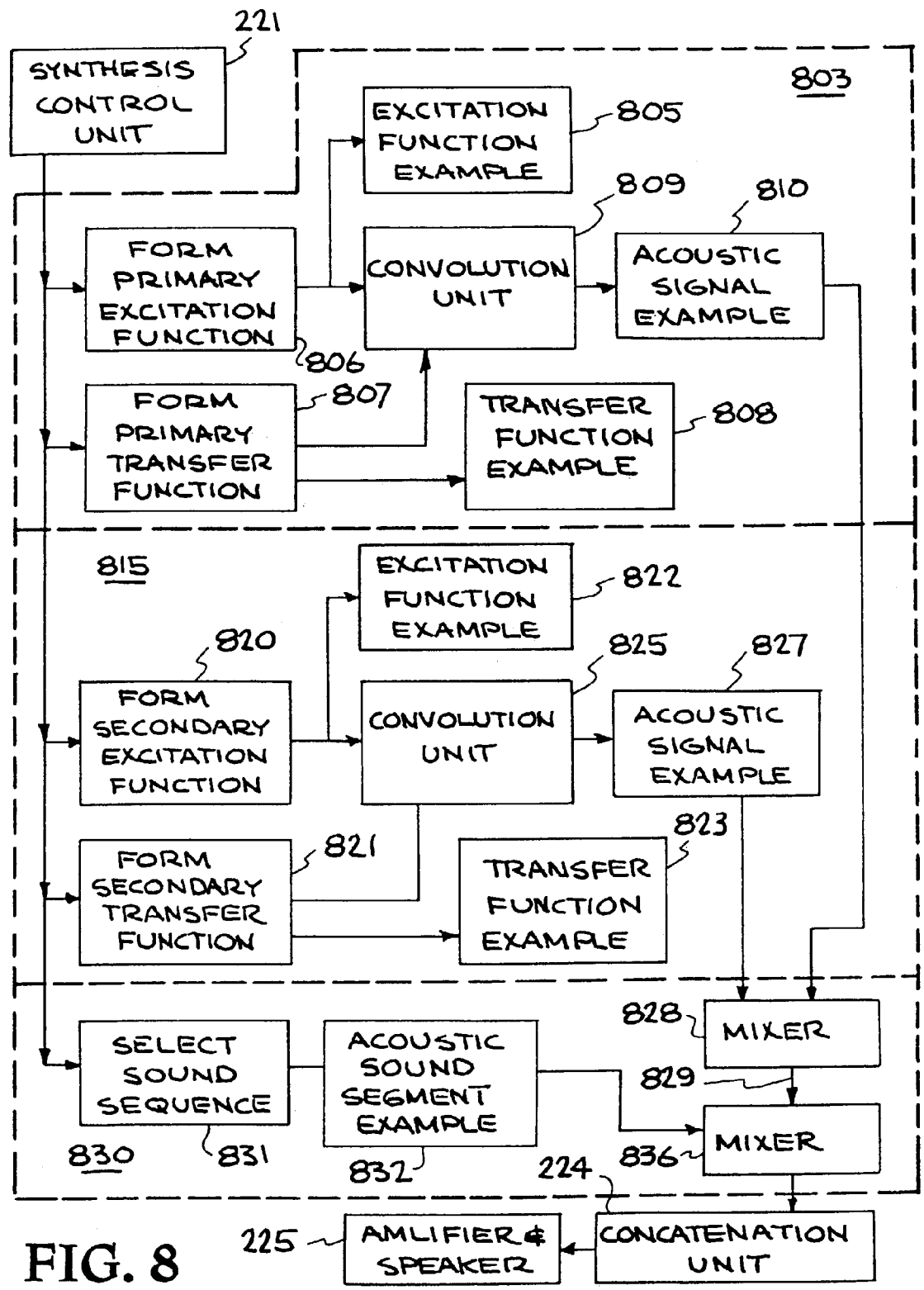
FIG. 8 is a dataflow diagram for synthesizing an acoustic signal.

FIG. 8 is a dataflow diagram 800 for synthesizing an acoustic signal. Sounds may be synthesized by the synthesis processor 223 and the concatenation unit 224 from feature vectors stored in memory. To begin, the synthesis control unit 221 receives synthesis instructions, from the synthesis control unit 221, in a standardized musical input stream format, such as MIDI (which is used for music), or other sound instruction sets. The instructions describe a set of sound segments, their sequence, a type of sound making device (e.g., a musical instrument or human), an excitation type, pitch values (i.e., the notes if a musical instrument is used), various sound amplitudes, damping rates, time durations, types of sound onsets, and inter-time frame connectivity.

For sounds that are best synthesized as a group rather than as a concatenated sound sequence, "expert" excitations and transformations are used. "Expert patterns" describe a complex amplitude, transfer function and excitation sequence, pitch modulation, which an expert musician might use. The process uses the procedure described in FIG. 2, but uses longer multi-period time frames to capture more complex information.

The synthesis processor 223 synthesizes acoustic signals in three basic stages, depending upon synthesized acoustic signal complexity. In a first stage 803, primary feature vectors are used to synthesize an acoustic signal. In a second stage 815, secondary acoustic simulations are added to the primary synthesized acoustic signal. In a third stage 830, pre-recorded/stored acoustic sounds may be added to the synthesized acoustic signal.

In the first stage 803, in step 806, the synthesis processor 223 retrieves a primary excitation function 805, according to the received synthesis instructions, by retrieving feature vector information stored in the memory 211. The synthesis processor 223 shortens or stretches the primary excitation function so as to fit the time frame. If necessary, the amplitude of the primary excitation function is either escalated, maintained, or dampened with time, as specified in the instructions. Small pitch deviations, sometimes called vibrato, can be added as per the instructions. For special cases, such as a rapid onset (i.e., attack), where many modes of one excitation are required, an excitation function describing a sharp onset can be used. Alternatively, a simple sharp excitation turn-on of a multiple mode excitation pattern or expert excitations may be used.

A continuous sound is produced by, concatenating a set of sounds over a specified number of time frames. Slow sound changes can be effected by slowly changing transfer function coefficients over several time frames, blending one type of sound into a next. Abrupt sound changes can be effected by changing the excitation amplitude abruptly, inserting silent periods, or altering the time frame, etc. Slow decays can be created by filtering a suitably long decaying excitation function with a transfer function filter.

In step 807, the synthesis processor 223 accesses the memory 211 and recalls a primary transfer function 808 and coefficients, which correspond to the selected instrument and the sound to be formed. Next, a convolution unit 809 in the synthesis processor 223 convolves the primary excitation function 805 with the primary transfer function 808 to synthesize a primary portion 810 of the acoustic signal. The first portion 810 of the acoustic signal is formed as a sequence of digital numbers representing an amplitude which varies with time.

In the second stage 815, in step 820, the synthesis processor 223 obtains a secondary excitation function 822, according to the received synthesis instructions, by retrieving feature vector information stored in the memory 211. The secondary excitation function 822 is often used to generate either periodic or chaotic sounds that are added to the primary portion of the acoustic signal to enhance the simulation quality of the desired acoustic signal. In step 821, the synthesis processor 223 accesses the memory 211 and recalls a secondary transfer function 823 and coefficients, corresponding to the selected sound to be produced. Next, in step 825, the secondary excitation function 822 is convolved with the secondary transfer function 823 to synthesize a second portion 827 of the acoustic signal. The synthesis processor 223 then synchronizes the first 810, and second portions 827 to the primary excitation time frame. A first mixer 828 adds the time varying amplitude of the first portion 810 of the acoustic signal to a time varying amplitude of the second portion 827 of the acoustic signal, forming an intermediate acoustic signal.

In the third stage 830, in step 831, the synthesis processor 223 may select a digitized acoustical sound sequence stored in the memory 211, according to the received synthesis instructions. A second mixer 836 would add this to the intermediate acoustic signal to create a final intermediate acoustic signal. As discussed above, the concatenation unit 224 links multiple sets of intermediate acoustic signals, having differing time frames, which the amplifier/speaker 225 broadcasts to the listener 226.

The concatenation unit 224 concatenates periodic and chaotic sounds from a present intermediate time frame sequence to the past frame sequences by using well known concatenation procedure for "smoothing" digital acoustic signals from previous time frames to the next. This process allows for creative modifications to analyzed data for example, by synthesizing a sound using a violin excitation and clarinet transfer function. Finally, multiple acoustic signals may be synthesized simultaneously, such as to simulate an orchestra, using parallel processing techniques in the synthesis processor 223.

FIG. 9A is a graph of an exemplary measured acoustic signal 902. The exemplary measured acoustic signal 902 actually shown is that of a violin being bowed on an open G-string.

FIG. 9B is a graph of an exemplary synthesized acoustic signal 904, corresponding to the exemplary measured acoustic signal 902. The exemplary synthesized acoustic signal 904 is a simulation of the violin being bowed on the open G-string. The synthesized signal 904 was experimentally created according to the method described above. The method included the steps of generating a polynomial filter, corresponding to a polynomial approximation of a violin transfer function with a G-string excitation, defined by a 58 pole and 7 zero set of ARMA coefficients. Several time segments of G-string bowing were used and the violin transfer function was estimated several times. Filter function coefficients, from the several time sequences, were averaged and stored. During synthesis, a stored sequence of a few cycles of bowed excitations of the open G-string on the violin were recalled from memory and concatenated to make a several second excitation sequence. The excitation sequence was digitally filtered by the polynomial filter, resulting in exemplary synthesized acoustic signal 904. The exemplary synthesized acoustic signal 904 was then converted to an analog signal and played over a loudspeaker. As shown in FIG. 9B, the exemplary synthesized acoustic signal 904 is a close match to the exemplary measured acoustic signal 904 in FIG. 9A. Subjective analysis determined that the synthesized signal 904 is of excellent quality as compared with the measured signal 902. The exemplary synthesized acoustic signal 904 captured low, rich sounds of the violin. During this exemplary synthesis, neither secondary excitation information nor additional stored sound information was used.

Figure 10:
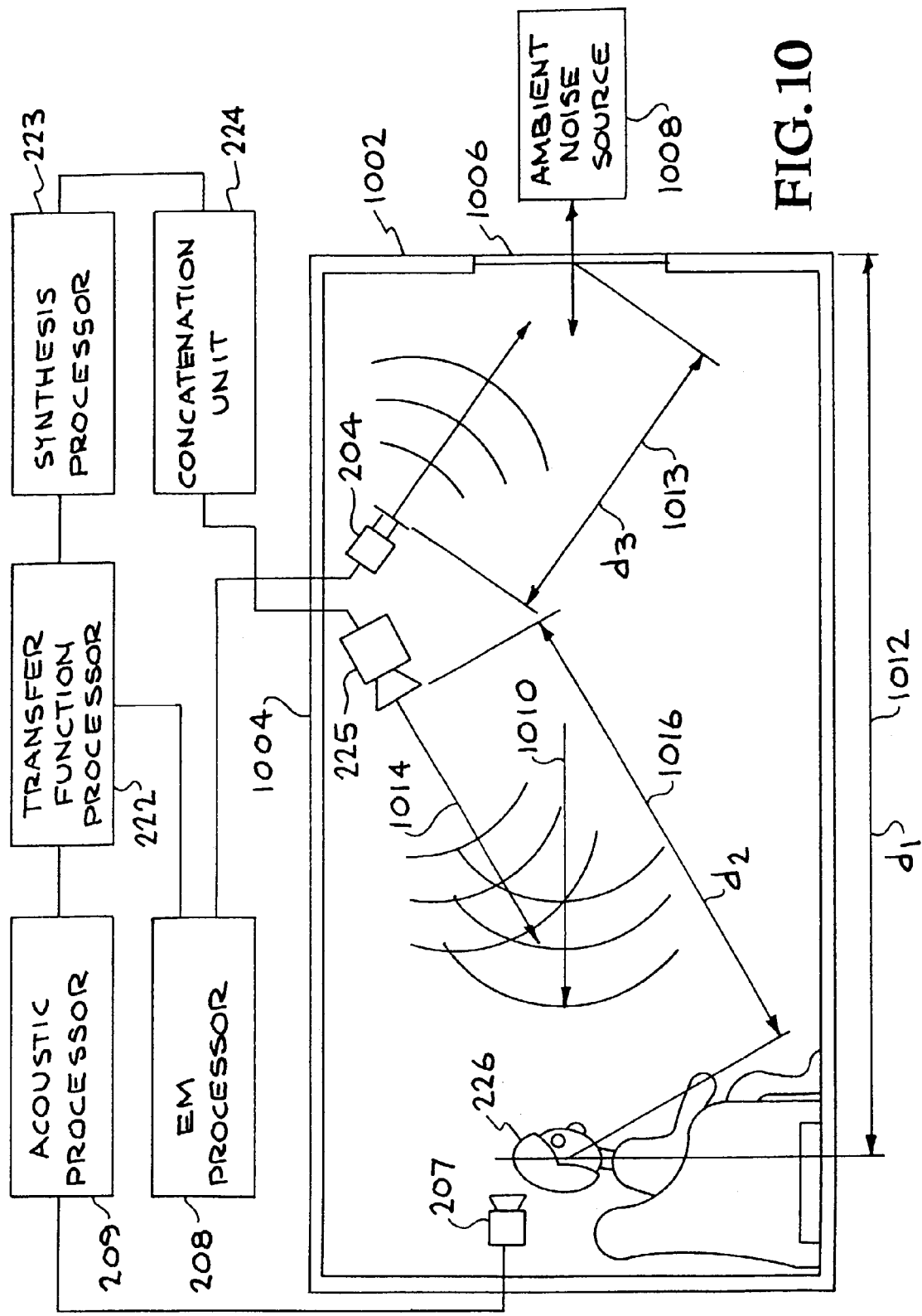
FIG. 10 is an exemplary application of the system to noise cancellation in a room.

FIG. 10 is an exemplary application of the system 200 to noise cancellation in a room 1002. In the room 1002, the EM sensor 204 is located on a ceiling 1004 of the room 1002. The EM sensor 204 is pointed downward toward a windowpane 1006 at an angle of about 35 degrees to a normal of the windowpane 1006. Since large smooth, non-conducting surfaces, such as the windowpane 1006 tend to be a poor reflectors of EM signals, attaching quarter-wavelength long metallic or transparent semiconducting strips, such as tin oxide, can substantially enhance the reflected EM signal. The windowpane 1006 (i.e., excitation source 1006) transmits ambient noise 1008 from outside of the room 1002 as incoming acoustic noise 1010.

The incoming noise 1010 can be canceled out using the system 200 according to the methods described above and the following details. Preferably the acoustic sensor 207 is located near the listener 226, at a distance (d1) 1012 from the excitation source 1006. Since the noise 1008 is usually chaotic in nature, a default time frame on the order of 0.1 to 1 second, for example, can be assigned. The default time frame is often chosen to capture a reverberation time of the room 1002. Together with the acoustic signal, processed by the acoustic processor 209, the transfer function processor 222 generates a transfer function and associated coefficients for the room 1002. Transfer function data for several default time frames, of fixed excitation time frames are averaged to obtain an accurate set of coefficients. During synthesis/cancellation, the excitation signal from the EM sensor 204 is formed into an excitation feature vector by the EM processor 208. Since computation speed is critical, the EM processor 208 preferably processes only short segments of the excitation signal at a time and routes corresponding short segments of the parameterized excitation function directly to the transfer function processor 222, by-passing the memory 211. Next, the synthesis processor 223 and the concatenation unit 224 operate to synthesize a canceling acoustic noise signal 1014. Sound is amplified as needed and the speaker 225 is positioned at a distance (d2) 1016 from the listener 226 and transmits the canceling acoustic noise signal 1014. The canceling acoustic noise signal 1014 cancels out the incoming noise 1010.

To most effectively cancel out the incoming noise 1010, the canceling acoustic noise signal 1014 may need to be fine tuned to account for various system 200 processing delays, amplitude variations, and changes in the room 1002 or the ambient noise source 1008. These "set-up" adjustments can be either manually effected by a user, or automatically effected by various well known adaptive acoustic algorithms, using a microphone to provide an error signal (see "Encyclopedia of Acoustics").

Figure 11:
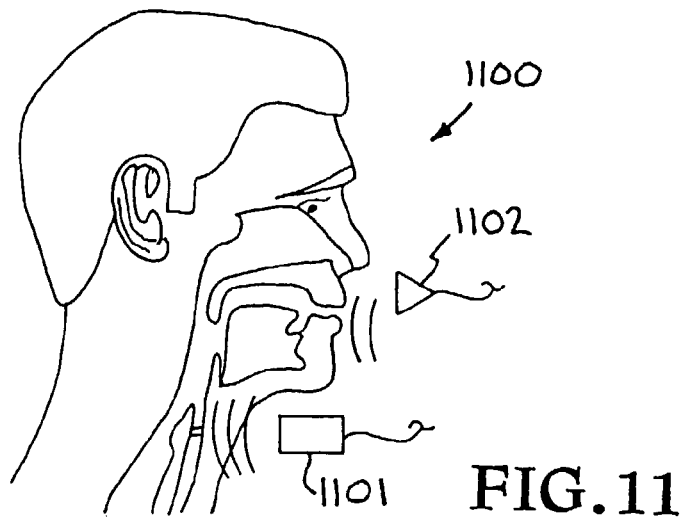
FIG. 11 is a pictorial diagram of a system representing another embodiment of the present invention.

Referring now to FIG. 11, a pictorial diagram of a system representing another embodiment of the present invention is shown. The system is designated generally by the reference numeral 1100. The system 1100 utilizes a coherent wave EM sensor 1101 measuring the movement of the vocal folds and the corresponding opening and closing of the space between the folds, called the glottis. These movements occur as voiced speech is produced. The vocal fold movement is an example of an auxiliary excitation source, whose movement can be measured using an EM sensor and then used to determine the primary excitation function, which is the air flow through the glottal opening between the vocal folds. An acoustic microphone 1102 measures corresponding acoustic speech signals. U.S. Pat. No. 5,729,694, entitled "Speech Coding, Reconstruction and Recognition Using Acoustics and Electromagnetic Waves" by Holzrichter and Ng, filed Feb. 6, 1996, is herein incorporated by reference and describes procedures for sound analysis and simulation based upon measuring excitations and acoustic signals from animate systems (e.g., humans) using ElectroMagnetic (EM) sensors and acoustic sensors. U.S. Pat. No. 5,729,694 also describes how simple mathematical functions, such as polynomials, sines or cosines, can model excitation sources, and how "all-pole" methods, such as Linear Prediction Coding (LPC) can be used. Most importantly, these methods describe how more accurate "pole-zero" methods are enabled by the EM sensor and acoustic sensor combination. These methods, such as Autoregressive Moving Average (ARMA), can model transfer functions with "zeros" at particular frequencies that occur in most acoustic systems. Also, incorporated by reference are the general methods of low power electromagnetic (EM) sensor design for inanimate and animate system motion measurements described in U.S. Pat. Nos. 5,345,471, 5,361,070, 5,573,012, 5,682,164, and 5,805,110 each by T. E. McEwan.

The system 1100 provides a method of characterizing a sound source, comprising the steps of characterizing excitations from the sound source; characterizing acoustic emissions from the sound source; and generating, from the excitations and the acoustic emissions, a function which represents the sound source. The system 1102 and the method incorporated and include the previously described information, particularly the information previously described in connection with FIGS. 1–10.

Figure 12:
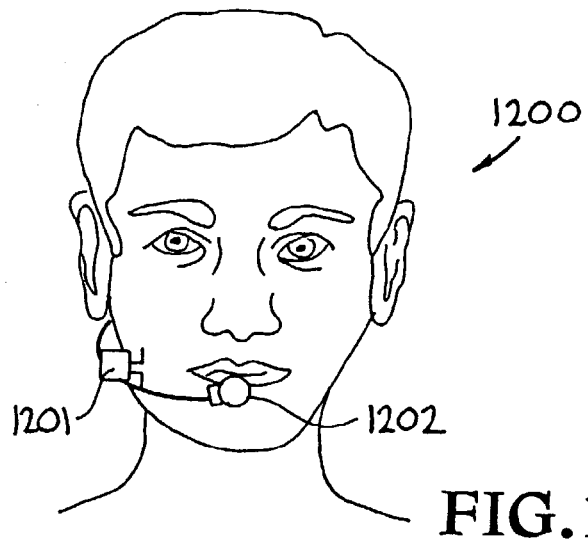
FIG. 12 is a pictorial diagram of a system representing another embodiment of the present invention.

Referring now to FIG. 12, a system representing another embodiment of the present invention is shown. The system is designated generally by the reference numeral 1200. An EM sensor 1201 is shown located on acoustic microphone boom, which measures external and internal cheek movements due to air pressure changes inside the oral cavity as voiced speech is being spoken. This is an example of an auxiliary excitation measurement that can be associated with the primary excitation function of human speech which is the air flow through the glottis. An acoustic microphone 1202 is held in front of the mouth and measures corresponding acoustic speech signals. The system 1200 and the method incorporated include the previously described information, particularly the information previously described in connection with FIGS. 1–11.

Figure 13:
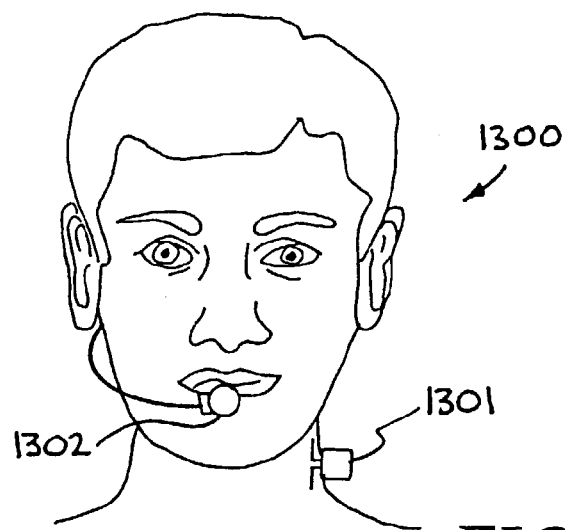
FIG. 13 is a pictorial diagram of a system representing another embodiment of the present invention.

Referring now to FIG. 13, a system representing another embodiment of the present invention is shown. The system is designated generally by the reference numeral 1300. An EM sensor 1301 is shown located on side of neck, measuring motions of the super-glottal vocal tract walls. This is an example of a type of auxiliary excitation, where the vocal tract walls move in response to the primary excitation which is the air flow and air pressure caused by the opening and closing of the vocal folds. An acoustic microphone 1202 measures corresponding acoustic speech signals. The system 1300 and the method incorporated and include the previously described information, particularly the information previously described in connection with FIGS. 1–12.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A method for canceling out acoustic signals from a sound source, comprising the steps of:
   generating an excitation function from excitations of the sound source;
   generating an acoustic function from acoustic emissions of the sound source;
   calculating a transfer function from the excitation function and the acoustic function;
   receiving cancellation instructions;
   convolving the excitation function with the transfer function to synthesize a canceling acoustic signal; and
   broadcasting the canceling acoustic signal proximate to the acoustic emissions.

2. A system for canceling out acoustic signals from a sound source, comprising:
   means for generating an excitation function from excitations of the sound source;
   means for generating an acoustic function from acoustic emissions of the sound source;
   means for calculating a transfer function from the excitation function and the acoustic function;
   means for receiving cancellation instructions;
   means for convolving the excitation function with the transfer function to synthesize a canceling acoustic signal; and
   means for broadcasting the canceling acoustic signal proximate to the acoustic emissions.

3. A computer-usable medium embodying computer program code for causing a computer to canceling out acoustic signals from a sound source, by performing the steps of:
   generating an excitation function from excitations of the sound source;
   generating an acoustic function from acoustic emissions of the sound source;
   calculating a transfer function from the excitation function and the acoustic function;
   receiving cancellation instructions;
   convolving the excitation function with the transfer function to synthesize a canceling acoustic signal; and
   broadcasting the canceling acoustic signal proximate to the acoustic emissions.

4. A system for canceling out acoustic signals from a sound source, comprising:
   an electromagnetic processor for generating an excitation function from excitations of the sound source;
   an acoustic processor for generating an acoustic function from acoustic emissions of the sound source;
   a transfer function processor, coupled to the electromagnetic processor and the acoustic processor, for calculating a transfer function from the excitation function and the acoustic function;
   a synthesis processor, coupled to the transfer function processor, for receiving cancellation instructions, for convolving the excitation function with the transfer function to synthesize a canceling acoustic signal; and
   a broadcasting unit, coupled to the synthesis processor, for broadcasting the canceling acoustic signal proximate to the acoustic emissions.

* * * * *